US 8,278,338 B2

(12) United States Patent
Sundermann et al.

(10) Patent No.: US 8,278,338 B2
(45) Date of Patent: Oct. 2, 2012

(54) SATURATED AND UNSATURATED 3-PYRIDYL-BENZOCYCLOALKYLMETHYL-AMINES FOR USE IN TREATING PAIN, DEPRESSION AND/OR ANXIETY

(75) Inventors: Bernd Sundermann, Aachen (DE); Hagen-Heinrich Hennies, Simmerath (DE); Klaus Schiene, Duesseldorf (DE); Petra Bloms-Funke, Wuerselen (DE); Werner Englberger, Stolberg (DE); Sven Frormann, Aachen (DE); Derek Saunders, Aachen (DE)

(73) Assignee: Gruenenthal GmbH, Aachen (DE)

( * ) Notice: Subject to any disclaimer, the term of this patent is extended or adjusted under 35 U.S.C. 154(b) by 1625 days.

(21) Appl. No.: 11/643,792

(22) Filed: Dec. 22, 2006

(65) Prior Publication Data

US 2007/0203192 A1    Aug. 30, 2007

Related U.S. Application Data

(63) Continuation of application No. PCT/EP2005/006624, filed on Jun. 20, 2005.

(30) Foreign Application Priority Data

Jun. 22, 2004 (DE) .................. 10 2004 030 099

(51) Int. Cl.
*A61K 31/4402* (2006.01)
*C07D 213/24* (2006.01)

(52) U.S. Cl. ........ 514/357; 546/329; 546/330; 546/334; 546/335; 546/337

(58) Field of Classification Search ............... 546/329, 546/330, 334, 335, 337; 514/357
See application file for complete search history.

(56) References Cited

U.S. PATENT DOCUMENTS

| | | | |
|---|---|---|---|
| 3,444,176 A | 5/1969 | Mohrbacher et al. | |
| 4,845,221 A | 7/1989 | Stack et al. | |
| 5,668,141 A | 9/1997 | Shiosaki et al. | |

FOREIGN PATENT DOCUMENTS

| | | |
|---|---|---|
| EP | 1 125 582 B1 | 8/2006 |
| JP | 2004-149429 A | 5/2004 |
| WO | WO 92/09577 | 6/1992 |
| WO | WO 99/58490 | 11/1999 |
| WO | WO 03/004485 A1 | 1/2003 |

OTHER PUBLICATIONS

Dorwald, Side Reactions in Organic Synthesis, 2005, Wiley: VCH Weinheim Preface, pp. 1-15 & Chapter 8, pp. 279-308.*
German Search Report dated Jan. 18, 2005 (Two (2) pages).
International Search Report dated Nov. 15, 2005 (Seven (7) pages).
David Dubuisson et al., *The Formalin Test: A Quantitative Study of the Analgesic Effects of Morphine, Meperidine, and Brain Stem Stimulation in Rats and Cats*, vol. No. 4, 1977, pp. 161-174.
Hans Lineweaver et al., *The Determination of Enzyme Dissociation Constants*, vol. 56, pp. 658-666; Aug. 18, 1933.
Martin Ch. Frink et al., *Influence of Tramadol on Neurotransmitter Systems of the Rat Brain*, Arzneim Forsch/Drug Res.46 (II), 11, pp. 1029-1036 (1996).
E. G. Gray et al., *The Isolation of Nerve Endings From Brain: An Electron-Microscopic Study of Cell Fragments Derived by Homogenization and Centrifugation* Journal Anatomy, vol. No. 96, pp. 79-82. (1962).
Yung-Chi Cheng et al., *Relationship Between the Inhibition Constant ($K_r$) and the Concentration of Inhibitor Which Causes 50 Per cent Inhibition ($I_{50}$) of an Enzymatic Reaction**, Biochemical Pharmacology vol. 22 pp. 3099-3108, (1973).
Andrew W. Goddard et al., *Principles of the Pharmacotherapy of anxiety disorders*, Neurobiology of Mental Illness, pp. 548-563 Oxford university Press, NY (1999).
Pal Pacher et al., *Current Trends in the Development of New Antidepressants*, Current Medicinal Chemistry, 2001, vol. 8, pp. 89-100.
S. H. Sindrup., *Antidepressants as Analgesics, Anesthesia Biologic Foundations*, Chapter 64, pp. 987-997 (1997).
A. Geronikaki et al, *Synthesis of Some Thiazole Derivatives With Prospective Local Anaesthetic Activity*, Pharmazie 1989, 44, p. 349.
J.E. Sumpton et al., The Annals of Pharmacotherapy, vol. 35, No. 5, pp. 557-559 (2001).
D. Mochizucki et al., Human Pharmacology: Clinical and Experimental, vol. 19, Issue S1, pp. 15-19 (2004).
Z. Magalas et al., European Journal of Pharmacology, vol. 528, pp. 103-109 (2005).
P. M. Sweetnam et al., Psychopharmacology, vol. 118, pp. 369-376 (1995).
J. G. P. Pires et al., Brazilian Journal of Medical and Biological Research, vol. 38, pp. 1867-1872 (2005, received: Jul. 2004).
K. B. Thor et al., American Society for Pharmacology and Experimental Therapeutics, vol. 274, Issue 2, pp. 1014-1024 (1995).
K. E. Andersson, Urology, vol. 55(5A), pp. 51-57 (2000).
D. A. Gillespie et al., J Gastroenterol Hepatol., vol. 8(2), pp. 168-173 (1993).
P. R. Saxena et al., Expert Opinion on Investigational Drugs, vol. 3, No. 5, pp. 513-523 (1994).
J. A. Nielsen et al., Am J Clin Nutr., vol. 55, pp. 185S-188S (1992).

* cited by examiner

Primary Examiner — Patricia Morris
(74) Attorney, Agent, or Firm — Crowell & Moring LLP

(57) ABSTRACT

Saturated and unsaturated 3-pyridyl-benzocycloalkylmethyl-amines=compounds corresponding to formula (I), wherein the various substituents have the meaning provided in the description, and pharmaceutical formulations containing these compounds and methods for producing these compounds and related pharmaceutical formulation, and to methods for treating or inhibiting pain, depression and/or anxiety states.

18 Claims, No Drawings

SATURATED AND UNSATURATED 3-PYRIDYL-BENZOCYCLOALKYLMETHYL-AMINES FOR USE IN TREATING PAIN, DEPRESSION AND/OR ANXIETY

CROSS-REFERENCE TO RELATED APPLICATIONS

This application is a continuation of International patent application Serial No. PCT/EP2005/006624 filed Jun. 20, 2005 which claims benefit to German patent application Serial No. 10 2004 030 099.2 filed Jun. 22, 2004, the entire disclosures of which are hereby incorporated in their entirety.

FIELD OF THE INVENTION

The present invention relates to saturated and unsaturated 3-pyridyl-benzocycloalkylmethyl-amines, to processes for their preparation, to pharmaceutical formulations containing these compounds and to the use of saturated and unsaturated 3-pyridyl-benzocycloalkylmethyl-amines in the preparation of pharmaceutical formulation and to methods of treating or inhibiting pain, depression and/or anxiety.

BACKGROUND OF THE INVENTION

The treatment of acute and chronic pain is of great importance in medicine. There is a worldwide need for highly effective therapies for treating acute and chronic pain in a targeted manner that is fair to the patient, which is to be understood as meaning the successful and satisfactory treatment of pain for the patient. This manifests itself in the large number of scientific works that have recently appeared in the field of applied analgesia or fundamental research into nociception.

SUMMARY OF THE INVENTION

Conventional opioids such as morphine are highly effective in the therapy of severe to very severe pain. However, their use is limited by the known side-effects, for example respiratory depression, vomiting, sedation, constipation and the development of tolerance. In addition, they are less effective in the case of neuropathic or incidental pain, from which tumour patients in particular suffer.

With the aim of improved treatment, combinations of opiates with monoamine serotonin (5-HT) and/or noradrenaline (NA) reuptake inhibitors are frequently used clinically in the case of chronic pain (inter alia inflammatory pain, tumour pain) (Sindrup, in: Yaksh, T. L. et al., Anesthesia. Biological foundations. Philadelphia: Lippincott-Raven, 1997, 987-997). In addition, because chronic pain is associated with anxiety or depression in a large number of patients, a substance having μ-opiate receptor agonist properties combined with clinically relevant serotonin and/or noradrenaline reuptake inhibition is particularly advantageous.

Noradrenaline and serotonin reuptake inhibitors are also used clinically for monotherapy in the case of chronic pain (Sindrup, in: Yaksh, T. L. et al., Anesthesia. Biological foundations. Philadelphia: Lippincott-Raven, 1997, 987-997). Monoamine reuptake inhibitors have an independent analgesic action, decreasing pain inhibition pathways being activated at the level of the spinal cord.

The use of monoamine reuptake inhibitors is limited by side-effects such as, for example, accommodation disturbances, serotonin syndrome or QT lengthening. There continues to be an urgent need for the treatment of chronic pain in particular in a manner that is fair to the patient.

Noradrenaline and serotonin reuptake inhibitors are widely used clinically in the treatment of depression and anxiety (Pacher, P., Kohegyi, E., Kecskemeti, V., Furst, S., Current Medicinal Chemistry 2001, 8, 89-100; Goddard, A. W., Coplan, J. D., Gorman, J. M., Charney, D. S., in: Neurobiology of mental illness, Charney, D. S., Nestler, E. J., Bunney, B. S. (eds.), Oxford University Press, New York, 1999, p. 548-563).

Depression is a disturbance of affectivity, in which a depressive syndrome is to the fore, depressive meaning associated with ill-feeling or in an unhappy mood. The depressive disorders include unipolar severe depression with or without mania, moderate depression, slight depression, dysthymia, melancholia, bipolar depression (bipolar disorders I, mania and severe depression; bipolar disorders II, hypomania and severe depression; cyclothymic personality disorders, hypomania) and mild depression. Anxiety is divided into generalised anxiety, panic attacks, obsessive compulsive disorders (OCD), social anxiety, simple phobias, agoraphobias, post-traumatic stress disorders (PTSD).

In general, the administration of monoamine reuptake inhibitors permits successful treatment in patients suffering from depression or anxiety. Nevertheless, about 30% of patients are refractory and relapse rates are high. Because of this limited success of therapy and the above-mentioned frequent side-effects of monoamine reuptake inhibitors, there is an urgent need for a successful treatment for depression and anxiety that is fair to the patient.

One of the objects underlying the invention was to provide novel compounds that are suitable for the therapy of pain, depression and/or anxiety. In addition, these compounds should exhibit as few as possible of the side-effects of monoamine reuptake inhibitors, such as, for example, accommodation disorders, serotonin syndrome or QT lengthening, or of opiates, such as, for example, respiratory depression, vomiting, sedation, constipation and the development of tolerance. Further objects consisted in the provision of novel active ingredients for the treatment of migraine, urinary incontinence, fibromyalgia, eating disorders, bulimia, hyperactivity, drug dependency, addiction and withdrawal, trichotillomania, Tourette's syndrome, skin diseases such as post-herpetic neuralgia and pruritus, psychoses, memory disorders, cognitive disorders and/or Alzheimer's disease.

It has now been found that derivatives of the general formula I below exhibit a high affinity for the μ-opiate receptor and/or inhibit the reuptake of noradrenaline and/or serotonin. The substances have pronounced antinociceptive, antidepressive and anxiolytic activities and are therefore suitable for the treatment of depression, anxiety and pain. The compounds according to the invention have in particular a potential for the therapy of chronic pain associated with depressive ill-feeling or anxiety. The substances are also suitable for the treatment of migraine, urinary incontinence, fibromyalgia, eating disorders, bulimia, hyperactivity, drug dependency, addiction and withdrawal, trichotillomania, Tourette's syndrome, skin diseases such as post-herpetic neuralgia and pruritus, psychoses, memory disorders, cognitive disorders and Alzheimer's disease.

Accordingly, the present invention provides saturated and unsaturated 3-pyridyl-benzocycloalkylmethyl-amines of the following general formula I, also in the form of their racemates, enantiomers, diastereoisomers, especially mixtures of their enantiomers or diastereoisomers, or in the form of an individual enantiomer or diastereoisomer, and also in the form of their free bases or of a salt formed with a physiologically acceptable acid:

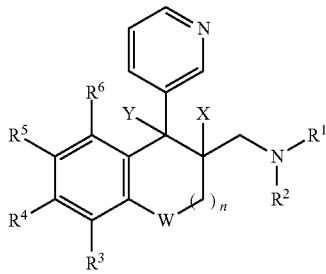

I wherein

W is CH$_2$, O, S, SO or SO$_2$ and n=from 0 to 3,

R$^1$ and R$^2$, independently of one another, are selected from H, C$_1$-C$_{10}$-alkyl, C$_2$-C$_{10}$-alkenyl or C$_3$-C$_{10}$-alkynyl, in each case branched or unbranched, mono- or poly-substituted or unsubstituted; C$_3$-C$_7$-cycloalkyl, saturated or unsaturated, mono- or poly-substituted or unsubstituted, or a corresponding heterocycle in which a carbon atom in the ring has been replaced by S, O or NR$^{3'}$, where R$^{3'}$ is selected from H, C$_1$-C$_{10}$-alkyl, C$_2$-C$_{10}$-alkenyl or C$_2$-C$_{10}$-alkynyl, in each case branched or unbranched, mono- or poly-substituted or unsubstituted;

alkylaryl, saturated or unsaturated, mono- or poly-substituted or unsubstituted; aryl, mono- or poly-substituted or unsubstituted;

or

R$^1$ and R$^2$ together form a C$_3$-C$_7$-cycloalkyl, saturated or unsaturated, mono- or poly-substituted or unsubstituted, or a corresponding heterocycle in which a carbon atom in the ring has been replaced by S, O or NR$^{4'}$, where R$^{4'}$ is selected from H, C$_1$-C$_{10}$-alkyl, C$_2$-C$_{10}$-alkenyl or C$_3$-C$_{10}$-alkynyl, in each case branched or unbranched, mono- or poly-substituted or unsubstituted;

and

R$^3$ to R$^6$, independently of one another, are selected from H or any desired radicals with the exception of further fused rings.

The term radicals within the scope of this invention is understood as meaning the substitution of at least one hydrogen radical by F, Cl, Br, I, CN, CF3, OCF3, NO2, C1-C10-alkyl, C2-C10-alkenyl or C3-C10-alkynyl, in each case branched or unbranched, mono- or poly-substituted or unsubstituted; C3-C7-cycloalkyl, saturated or unsaturated, mono- or poly-substituted or unsubstituted, or a corresponding heterocycle in which a carbon atom in the ring has been replaced by S, O or NR$^{5'}$, where R$^{5'}$ is selected from H, C$_1$-C$_{10}$-alkyl, C$_2$-C$_{10}$-alkenyl or C$_2$-C$_{10}$-alkynyl, in each case branched or unbranched, mono- or poly-substituted or unsubstituted;

OR$^{6'}$, OC(O)R$^{6'}$, OC(S)R$^{6'}$, C(O)R$^{6'}$, C(O)OR$^{6'}$, C(S)R$^{6'}$, C(S)OR$^{6'}$, SR$^{6'}$, S(O)R$^{6'}$ or S(O$_2$)R$^{6'}$, where R$^{6'}$ is selected from H, C$_1$-C$_{10}$-alkyl, C$_2$-C$_{10}$-alkenyl or C$_2$-C$_{10}$-alkynyl, in each case branched or unbranched, mono- or poly-substituted or unsubstituted; C$_3$-C$_7$-cycloalkyl, saturated or unsaturated, mono- or poly-substituted or unsubstituted, or a corresponding heterocycle in which a carbon atom in the ring has been replaced by S, O or NR$^7$, where R$^7$ is selected from H, C$_1$-C$_{10}$-alkyl, C$_2$-C$_{10}$-alkenyl or C$_3$-C$_{10}$-alkynyl, in each case branched or unbranched, mono- or poly-substituted or unsubstituted;

alkylaryl, saturated or unsaturated, mono- or poly-substituted or unsubstituted; aryl or heteroaryl, in each case mono- or poly-substituted or unsubstituted;

NR$^8$R$^9$, C(O)NR$^8$R$^9$ or S(O$_2$)NR$^8$R$^9$ wherein R$^8$ and R$^9$, independently of one another, are selected from:

H, C$_1$-C$_{18}$-alkyl, C$_2$-C$_{18}$-alkenyl or C$_3$-C$_{18}$-alkynyl, in each case branched or unbranched, mono- or poly-substituted or unsubstituted; C$_3$-C$_7$-cycloalkyl, saturated or unsaturated, mono- or poly-substituted or unsubstituted, or a corresponding heterocycle in which a carbon atom in the ring has been replaced by S, O or NR$^{10}$, where R$^{10}$ is selected from H, C$_1$-C$_{10}$-alkyl, C$_2$-C$_{10}$-alkenyl or C$_3$-C$_{10}$-alkynyl, in each case branched or unbranched, mono- or poly-substituted or unsubstituted;

alkylaryl, saturated or unsaturated, mono- or poly-substituted or unsubstituted; aryl or heteroaryl, in each case mono- or poly-substituted or unsubstituted;

or

R$^8$ and R$^9$ together form a C$_3$-C$_7$-cycloalkyl, saturated or unsaturated, mono- or poly-substituted or unsubstituted, or a corresponding heterocycle in which a carbon atom in the ring has been replaced by S, O or NR$^{10}$, where R$^{10}$ is selected from H, C$_1$-C$_{10}$-alkyl, C$_2$-C$_{10}$-alkenyl or C$_3$-C$_{10}$-alkynyl, in each case branched or unbranched, mono- or poly-substituted or unsubstituted;

alkylaryl, aryl or heteroaryl, in each case mono- or poly-substituted or unsubstituted.

In the general formula I, Y is selected from H and OH when X is simultaneously H, or X and Y together form a bond.

Within the scope of this invention, the term "substituted" is understood as meaning the substitution of a hydrogen radical by F, Cl, Br, I, NH$_2$, SH or OH, OCH$_3$, polysubstituted radicals being understood to be radicals that are polysubstituted either on different atoms or on the same atoms, for example trisubstituted on the same carbon atom, as in the case of CF$_3$, or in different positions, as in the case of —CH(OH)—CH=CH—CHCl$_2$.

The expression "C$_1$-C$_{10}$-alkyl" within the scope of this invention denotes hydrocarbons having from 1 to 10 carbon atoms. Examples which may be mentioned include methyl, ethyl, propyl, isopropyl, n-butane, sec.-butyl, tert.-butyl, n-pentane, neopentyl, n-hexane, n-heptane, n-octane, n-nonane, n-decane, unsubstituted or mono- or poly-substituted.

The expressions "C$_2$-C$_{10}$-alkenyl" and "C$_2$-C$_{10}$-alkynyl" within the scope of this invention denote hydrocarbons having from 2 to 10 carbon atoms. Examples which may be mentioned include ethenyl, propenyl, butenyl, pentenyl, hexenyl, heptenyl, octenyl, unsubstituted or mono- or poly-substituted, and ethynyl, propynyl, butynyl, pentynyl, hexynyl, heptynyl, octynyl, unsubstituted or mono- or poly-substituted.

The expression C$_3$-C$_7$-cycloalkyl within the scope of this invention denotes cyclic hydrocarbons having from 3 to 7 carbon atoms. Examples which may be mentioned include cyclopropyl, cyclobutyl, cyclopentyl, cyclohexyl, cycloheptyl, cyclohexenyl or cycloheptenyl, saturated or unsaturated, unsubstituted or mono- or poly-substituted. Within the scope of the invention, a "corresponding heterocycle" is understood as meaning a $C_3$-$C_7$-cycloalkyl in which at least one carbon atom in the ring has been replaced by S, O or N. Examples thereof which may be mentioned include pyrrolidine, pyran, thiolane, piperidine and tetrahydrofuran.

The expression "aryl" within the scope of this invention denotes phenyls or naphthyls.

The expression "alkylaryl" within the scope of this invention denotes aryls substituted by $C_1$-$C_{10}$-alkyls, the expressions aryl and alkyl having the same meaning as above.

The expression "heteroaryl" within the scope of this invention denotes 5- or 6-membered aromatic compounds which are optionally provided with a fused aryl system and contain one or two hetero atoms from the group nitrogen, oxygen and/or sulfur. Within this group, examples which may be mentioned include furan, thiophene, pyrrole, pyridine, pyrimidine, quinoline, isoquinoline, phthalazine and quinazoline.

The term of the salt formed with a physiologically acceptable acid is understood within the scope of this invention as meaning salts of the particular active ingredient with inorganic or organic acids which are physiologically acceptable—especially when used in humans and/or mammals.

Preference is given to compounds of the general formula I in which n<3. Particular preference is given to compounds of the general formula I in which W=$CH_2$ and n<3.

Very particular preference is given to compounds of the general formula I in which W=$CH_2$, n<3, $R^1$ and $R^2$=methyl and $R^5$ and $R^6$=H.

Preference is given in turn to the following compounds according to the invention and their salts:

2-dimethylaminomethyl-1-pyridin-3-yl-indan-1-ol and the corresponding hydrochloride (polar diastereoisomer) (1)
2-dimethylaminomethyl-1-pyridin-3-yl-indan-1-ol and the corresponding hydrochloride (non-polar diastereoisomer) (2)
dimethyl-(3-pyridin-3-yl-1H-inden-2-ylmethyl)-amine and the corresponding hydrochloride (3)
dimethyl-(1-pyridin-3-yl-indan-2-ylmethyl)-amine and the corresponding hydrochloride (4)
2-dimethylaminomethyl-5-methoxy-1-pyridin-3-yl-indan-1-ol and the corresponding hydrochloride (polar and non-polar diastereoisomer) (5)
(6-methoxy-3-pyridin-3-yl-1H-inden-2-ylmethyl)-dimethyl-amine and the corresponding hydrochloride (6)
2-dimethylaminomethyl-1-pyridin-3-yl-3H-inden-5-ol and the corresponding hydrochloride (7)
2-dimethylaminomethyl-1-pyridin-3-yl-1,2,3,4-tetrahydro-naphthalen-1-ol and the corresponding hydrochloride (polar and non-polar diastereoisomer) (8)
dimethyl-(1-pyridin-3-yl-3,4-dihydro-naphthalen-2-ylmethyl)-amine and the corresponding hydrochloride (9)
dimethyl-(1-pyridin-3-yl-1,2,3,4-tetrahydro-naphthalen-2-ylmethyl)-amine and the corresponding hydrochloride (10)
6-dimethylaminomethyl-5-pyridin-3-yl-6,7,8,9-tetrahydro-5H-benzocyclohepten-5-ol and the corresponding hydrochloride (11)
dimethyl-(5-pyridin-3-yl-8,9-dihydro-7H-benzocyclohepten-6-ylmethyl)-amine and the corresponding hydrochloride (12)
4-dimethylaminomethyl-5-pyridin-3-yl-2,3,4,5-tetrahydro-benzo[b]thiepin-5-ol and the corresponding hydrochloride (polar diastereoisomer) (13)
4-dimethylaminomethyl-5-pyridin-3-yl-2,3,4,5-tetrahydro-benzo[b]thiepin-5-ol and the corresponding hydrochloride (non-polar diastereoisomer) (14)
dimethyl-(5-pyridin-3-yl-2,3-dihydro-benzo[b]thiepin-4-ylmethyl)-amine and the corresponding hydrochloride (15)
dimethyl-(1-oxo-5-pyridin-3-yl-2,3-dihydro-1H-1λ4-benzo[b]thiepin-4-ylmethyl)-amine and the corresponding hydrochloride (16)
4-dimethylaminomethyl-1,1-dioxo-5-pyridin-3-yl-2,3,4,5-tetrahydro-1H-1λ6-benzo[b]thiepin-5-ol and the corresponding hydrochloride (17)
2-dimethylaminomethyl-5-fluoro-1-pyridin-3-yl-indan-1-ol and the corresponding hydrochloride (polar and non-polar diastereoisomer) (18)
(6-fluoro-3-pyridin-3-yl-1H-inden-2-ylmethyl)-dimethyl-amine and the corresponding hydrochloride (19)
2-dimethylaminomethyl-1-pyridin-3-yl-5-trifluoromethoxy-indan-1-ol and the corresponding hydrochloride (polar and non-polar diastereoisomer) (20)
dimethyl-(3-pyridin-3-yl-6-trifluoromethoxy-1H-inden-2-ylmethyl)-amine and the corresponding hydrochloride (21)
2-dimethylaminomethyl-1-pyridin-3-yl-5-trifluoromethyl-indan-1-ol and the corresponding hydrochloride (polar and non-polar diastereoisomer) (22)
dimethyl-(3-pyridin-3-yl-6-trifluoromethyl-1H-inden-2-ylmethyl)-amine and the corresponding hydrochloride (23)
4-dimethylaminomethyl-5-pyridin-3-yl-2,3,4,5-tetrahydro-benzo[b]oxepin-5-ol and the corresponding hydrochloride (non-polar diastereoisomer) (24)
4-dimethylaminomethyl-5-pyridin-3-yl-2,3,4,5-tetrahydro-benzo[b]oxepin-5-ol and the corresponding hydrochloride (polar diastereoisomer) (25)
dimethyl-(5-pyridin-3-yl-2,3-dihydro-benzo[b]oxepin-4-ylmethyl)-amine and the corresponding hydrochloride (26)
3-dimethylaminomethyl-4-pyridin-3-yl-chroman-4-ol and the corresponding hydrochloride (non-polar diastereoisomer) (27)
3-dimethylaminomethyl-4-pyridin-3-yl-chroman-4-ol and the corresponding hydrochloride (polar diastereoisomer) (28)
dimethyl-(4-pyridin-3-yl-2H-chromen-3-ylmethyl)-amine and the corresponding hydrochloride (29)
3-dimethylaminomethyl-4-pyridin-3-yl-thiochroman-4-ol and the corresponding hydrochloride (non-polar diastereoisomer) (30)
3-dimethylaminomethyl-4-pyridin-3-yl-thiochroman-4-ol and the corresponding hydrochloride (polar diastereoisomer) (31)
dimethyl-(4-pyridin-3-yl-2H-thiochromen-3-ylmethyl)-amine and the corresponding hydrochloride (32)
2-dimethylaminomethyl-6-methoxy-1-pyridin-3-yl-indan-1-ol and the corresponding hydrochloride (non-polar diastereoisomer) (33)
2-dimethylaminomethyl-6-methoxy-1-pyridin-3-yl-indan-1-ol and the corresponding hydrochloride (polar diastereoisomer) (34)
(5-methoxy-3-pyridin-3-yl-1H-inden-2-ylmethyl)-dimethyl-amine and the corresponding hydrochloride (35)
2-dimethylaminomethyl-5-methoxy-1-pyridin-3-yl-1,2,3,4-tetrahydro-naphthalen-1-ol and the corresponding hydrochloride (non-polar diastereoisomer) (36)
2-dimethylaminomethyl-5-methoxy-1-pyridin-3-yl-1,2,3,4-tetrahydro-naphthalen-1-ol and the corresponding hydrochloride (polar diastereoisomer) (37)
(5-methoxy-1-pyridin-3-yl-3,4-dihydro-naphthalen-2-ylmethyl)-dimethyl-amine and the corresponding hydrochloride (38)
6-dimethylaminomethyl-5-pyridin-3-yl-7,8-dihydro-naphthalen-1-ol and the corresponding hydrochloride (39).

From this list, particular preference is in turn given to the compounds:

dimethyl-(3-pyridin-3-yl-1H-inden-2-ylmethyl)-amine and the corresponding hydrochloride (3)

(6-methoxy-3-pyridin-3-yl-1H-inden-2-ylmethyl)-dimethyl-amine and the corresponding hydrochloride (6)

2-dimethylaminomethyl-1-pyridin-3-yl-3H-inden-5-ol and the corresponding hydrochloride (7)

6-dimethylaminomethyl-5-pyridin-3-yl-6,7,8,9-tetrahydro-5H-benzocyclohepten-5-ol and the corresponding hydrochloride (11)

dimethyl-(5-pyridin-3-yl-8,9-dihydro-7H-benzocyclohepten-6-ylmethyl)-amine and the corresponding hydrochloride (12)

(6-fluoro-3-pyridin-3-yl-1H-inden-2-ylmethyl)-dimethyl-amine and the corresponding hydrochloride (19)

dimethyl-(3-pyridin-3-yl-6-trifluoromethoxy-1H-inden-2-ylmethyl)-amine and the corresponding hydrochloride (21)

(5-methoxy-1-pyridin-3-yl-3,4-dihydro-naphthalen-2-ylmethyl)-dimethyl-amine and the corresponding hydrochloride (38)

6-dimethylaminomethyl-5-pyridin-3-yl-7,8-dihydro-naphthalen-1-ol and the corresponding hydrochloride (39).

The present invention further provides a process for the preparation of saturated and unsaturated 3-pyridyl-benzocycloalkylmethyl-amines of the general formula I indicated above.

3-Pyridyl-benzocycloalkylmethyl-amines of the general formula I are prepared by first reacting cycloalkanones of the general formula II with immonium salts of formula III or with paraformaldehyde and an amine of formula IV. Instead of the immonium salts of formula III it is also possible to use the reagents conventionally employed for their preparation, for example bis-(dimethylamino)-methane and acetyl chloride, in a manner known per se (A. Geronikaki et al. Pharmazie 1989, 44, 349). $R^{10}$ has a meaning analogous to $R^1$, $R^{11}$ has a meaning analogous to $R^2$. Cycloalkanones of the general formula II are either available commercially or can be prepared by processes known to the person skilled in the art.

The Mannich bases so obtained are then reacted with an organometallic compound of formula V in which Z represents lithium. The reaction of the Mannich bases with an organolithium compound of formula V in which Z represents Li can be carried out in an aliphatic ether, for example diethyl ether and/or tetrahydrofuran, at temperatures of between −70° C. and 60° C. In the case where either $R^{10}$ or $R^{11}$ is hydrogen or $R^{10}$ and $R^{11}$ are simultaneously hydrogen, compounds of the general formula III or IV in which $R^{10}$ or $R^{11}$ or $R^{10}$ and $R^{11}$ represent(s) a benzyl radical are used in the Mannich reaction. The benzyl radical is removed at a suitable point in the reaction sequence by reaction of the corresponding compounds with catalytically activated hydrogen, the catalyst used being platinum or palladium absorbed on a carrier material such as activated carbon.

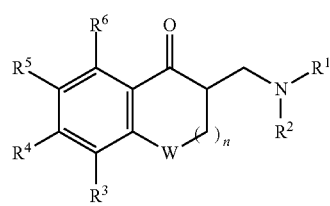

II

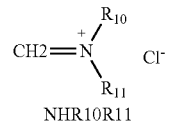

III

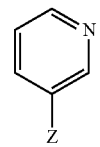

V

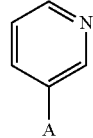

VI

Compounds of formula V in which Z represents lithium or magnesium halide can be obtained by halogen-lithium exchange by reaction of halogen compounds of formula VI in which A represents Cl, Br or I with, for example, n-butyl-lithium/hexane solution. Compounds of formula V can also be reacted with compounds of formula II in the presence of, for example, cerium(III) halide. In this manner there are first obtained products of the general formula VII in which $R^{10}$ has a meaning analogous to $R^1$ and $R^{11}$ has a meaning analogous to $R^2$. The compounds of formula IX are obtained by reaction of compounds of the general formula VII with thionyl chloride and subsequent basic working up. In some cases there is obtained a mixture of compounds of the general formulae VIII and IX in which $R^{10}$ has a meaning analogous to $R^1$ and $R^{11}$ has a meaning analogous to $R^2$. These can be separated by column chromatography or by crystallisation. Compounds of the general formula IX can be obtained specifically by reaction of compounds of the general formula VII with strong acids, e.g. hydrochloric acid or hydrobromic acid. Hydrobromic acid can preferably be used for that purpose if the demethylation of a methoxy radical $R^3$ to $R^6$ is desired at the same time. Alternatively, for compounds of the general formula IX it is possible in a subsequent reaction step to apply other processes, known to the person skilled in the art, for the demethylation of a methoxy radical $R^3$ to $R^6$, such as, for example, heating in the presence of an excess of diisobutylaluminium hydride in, for example, toluene or using diphenylphosphine and an alkyllithium compound in, for example, toluene/tetrahydrofuran.

Subsequent hydrogenolytic cleavage of compounds of the general formula VIII or hydrogenation of compounds of the general formula IX in which $R^{10}$ has a meaning analogous to $R^1$ and $R^{11}$ has a meaning analogous to $R^2$ with catalytically activated hydrogen, the catalyst used being platinum or palladium absorbed on a carrier material such as activated carbon, yields compounds of formula X in which $R^{10}$ has a meaning analogous to $R^1$ and $R^{11}$ has a meaning analogous to $R^2$. The hydrogenation is carried out in a solvent such as ethyl acetate or a $C_1$-$C_4$-alkyl alcohol at pressures of from 0.1 to 10 bar and temperatures of from 20° C. to 80° C.

If W is S, these compounds can be converted at a suitable point in the reaction sequence into the corresponding SO or $SO_2$ compounds using an oxidising agent such as $H_2O_2$.

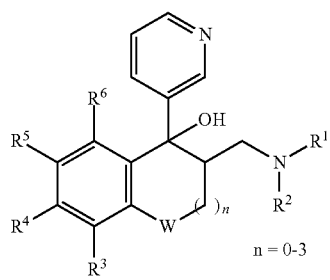

VII

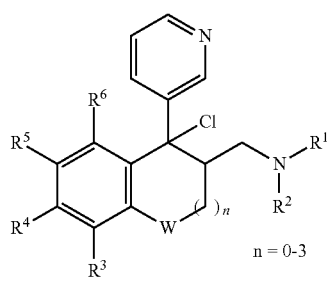

VIII

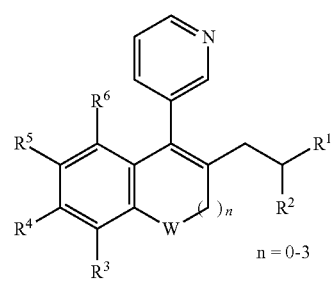

IX

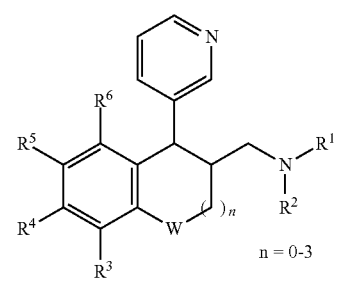

X

An alternative process for the preparation of unsaturated 3-pyridyl-benzocycloalkylmethyl-amines of the general formula I indicated above in which X and Y together form a bond is the transition-metal-catalysed cross-coupling of compounds of the general formula XI in which G2 is Cl, Br, I, Sn(alkyl)3 or OSO2CF3 with compounds of the general formula XII in which G1 is Cl, Br, I or B(ORx)2, where Rx is selected from H or alkyl, it being possible for the reaction to be carried out with or without a base and with or without a ligand. An example thereof is the Suzuki coupling of compounds of the general formula XI in which G2 represents OSO2CF3 with compounds of the general formula XII in which $G_1$ represents B(Oalkyl)$_2$ in the presence of palladium (II) acetate, a phosphine ligand and a base.

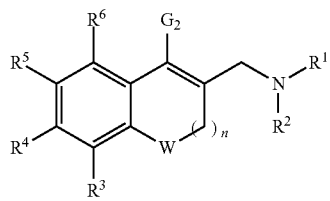

XI

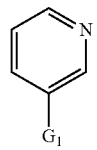

XII

A further alternative process for the preparation of unsaturated 3-pyridyl-benzocycloalkylmethyl-amines of the general formula I indicated above in which X and Y together form a bond and in which W is O or S and n=1 is the treatment of ortho-halo-substituted phenols/thiophenols (where Hal is selected from Br, I, OSO2CF3) of the general formula XIII with substituted propargylamines of the general formula XIV or with propargyl alcohols or their derivatives of the general formula XV (where Ro is selected from H or a protecting group), e.g. in the presence of dichlorobis(triphenylphosphine)palladium(II), copper(I) iodide and triethylamine. In the case of the propargyl alcohols or their derivatives of the general formula XV, the function ORo is converted in a subsequent reaction step into the amino function NR$^1$R$^2$ according to processes known to the person skilled in the art.

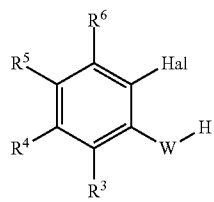

XIII

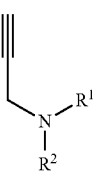

XIV

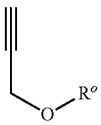

XV

Under the mentioned reaction conditions, OH, SH and NH$_2$ groups may enter into undesirable secondary reactions. It is therefore preferable to provide them with protecting groups, or in the case of NH$_2$ replace it with NO$_2$, and remove the protecting group, or reduce the NO$_2$ group, in the last reaction step. The invention therefore further provides a modification of the above-described process in which at least one OH group present in formula I has been replaced by a OSi(Ph)$_2$tert.but. group, at least one SH group has been replaced by a S-p-methoxybenzyl group and/or at least one NH$_2$ group has been replaced by a NO$_2$ group and, when the entire reaction sequence is complete, a OSi(Ph)$_2$tert.butyl group is removed with tetrabutylammonium fluoride in tetrahydrofuran and/or at least one p-methoxybenzyl group is removed with a metal amine, preferably sodium amine, and/or at least one NO$_2$ group is reduced to NH$_2$.

Furthermore, under certain circumstances carboxylic acid groups or thiocarboxylic acid groups are not stable under the conditions of the butyllithium reaction, so that it is preferable to react the methyl esters thereof and to saponify the process product from the butyllithium reaction in the last reaction step using KOH solution or NaOH solution in methanol at from 40° C. to 60° C. The invention therefore further provides a modification of the above-described processes in which, following the butyllithium reaction, a process product having at least one C(O)OCH$_3$ and/or C(S)OCH$_3$ group is saponified using KOH solution or NaOH solution in methanol at from 40° C. to 60° C.

Purification of the compounds obtained in the individual reaction sequences is carried out by crystallisation or column chromatography.

The compounds of formula I can be converted into their salts in a manner known per se with physiologically acceptable acids such as hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, maleic acid, glutamic acid and/or aspartic acid. The salt formation is preferably carried out in a solvent such as diisopropyl ether, alkyl acetate, acetone and/or 2-butanone. For the preparation of the hydrochlorides, trimethylchlorosilane in aqueous solution is particularly suitable.

The saturated and unsaturated 3-pyridyl-benzocycloalkyl-methyl-amines of the general formula I according to the invention are toxicologically harmless and are therefore suitable as pharmaceutical active ingredients in medicaments.

The present invention therefore further provides medicaments comprising at least one compound of the general formula I according to the invention and, optionally, physiologically acceptable auxiliary substances. The medicaments according to the invention are preferably suitable for the control of pain (in particular chronic pain, neuropathic pain, inflammatory pain), migraine, fibromyalgia or for the treatment of depression (unipolar, severe depression with and without mania, moderate depression, slight depression, melancholia, bipolar depression; bipolar disorders I (mania and severe depression), bipolar disorders II (hypomania and severe depression), cyclothymic personality disorders (hypomania and mild depression), subtypes), anxiety (subtypes generalised anxiety, panic attacks, obsessive compulsive disorders, social anxiety disorder, phobias, PSTD), sleep disorders, urinary incontinence (stress and urge), eating disorders, bulimia, attention deficit hyperactivity disorder, addiction and dependency, trichotillomania, Tourette's syndrome, skin diseases such as post-herpetic neuralgia and pruritus, psychoses, memory disorders, cognitive disorders and/or Alzheimer's disease.

The present invention relates also to the use of at least one compound of the general formula I in the preparation of a medicament for the control of pain (in particular chronic pain, neuropathic pain, inflammatory pain), migraine, fibromyalgia or for the treatment of depression (unipolar, severe depression with and without mania, moderate depression, slight depression, melancholia, bipolar depression; bipolar disorders I (mania and severe depression), bipolar disorders II (hypomania and severe depression), cyclothymic personality disorders (hypomania and mild depression), subtypes), anxiety (subtypes generalised anxiety, panic attacks, obsessive compulsive disorders, social anxiety disorder, phobias, PSTD), sleep disorders, urinary incontinence (stress and urge), eating disorders, bulimia, attention deficit hyperactivity disorder, addiction and dependency, trichotillomania, Tourette's syndrome, skin diseases such as post-herpetic neuralgia and pruritus, psychoses, memory disorders, cognitive disorders and/or Alzheimer's disease.

The medicaments according to the invention may be present in the form of liquid, semi-solid or solid medicament forms, for example in the form of injection solutions, drops, juices, syrups, sprays, suspensions, tablets, patches, capsules, plasters, suppositories, ointments, creams, lotions, gels, emulsions, aerosols or in multiparticulate form, for example in the form of pellets or granules, and may also be administered as such.

In addition to at least one compound of the general formula I according to the invention, the medicaments according to the invention usually comprise further physiologically acceptable pharmaceutical auxiliary substances, which are preferably selected from the group consisting of carriers, fillers, solvents, diluents, surface-active substances, colourings, preservatives, disintegrators, glidants, lubricants, flavourings and binders.

The choice of physiologically acceptable auxiliary substances and the amounts thereof to be used are dependent on whether the medicament is to be administered orally, subcutaneously, parenterally, intravenously, intraperitoneally, intradermally, intramuscularly, intranasally, buccally, rectally or locally, for example to infections of the skin, the mucous membranes and of the eyes. Formulations in the form of tablets, dragées, capsules, granules, pellets, drops, juices and syrups are suitable for oral administration; solutions, suspensions, readily reconstitutable dry formulations and sprays are suitable for parenteral and topical administration and for administration by inhalation. Compounds of the general formula I according to the invention in a depot, in dissolved form or in a plaster, optionally with the addition of agents which promote penetration through the skin, are suitable formulations for percutaneous administration. Preparation forms which can be used orally or percutaneously can also release the compounds of the general formula I according to the invention in a delayed manner.

The preparation of the medicaments according to the invention can be carried out with the aid of conventional agents, devices, methods and processes known to the person skilled in the art, as are described, for example, in "Remington's Pharmaceutical Sciences"; ed. A. R. Gennaro, 17th Edition, Mack Publishing Company, Easton, Pa. (1985), especially in Part 8, Chapters 76 to 93. The corresponding literature description is incorporated herein by reference and is to be regarded as part of the disclosure.

The amount of the particular saturated or unsaturated 3-pyridyl-benzocycloalkylmethyl-amines of the general formula I according to the invention to be administered to the patients can vary and is dependent, for example, on the weight or age of the patient and on the mode of administration, the indication and the severity of the disease. From 0.005 to 500 mg/kg, preferably from 0.05 to 5 mg/kg body weight of the patient of at least one compound of the general formula I according to the invention are usually administered.

The invention also relates further to a method of treating pain, depression and/or anxiety, in which the compounds used according to the invention are employed.

Certain embodiments of the present invention may be further understood by reference to the following specific examples. These examples and the terminology used herein are for the purpose of describing particular embodiments only and are not intended to be limiting.

EXAMPLES

The following examples show compounds according to the invention and their preparation, and activity studies carried out therewith.

The following apply in general:

The yields of the compounds prepared have not been optimised.

All temperatures are uncorrected.

Silica gel 60 (0.040-0.063 mm) from E. Merck, Darmstadt, was employed as the stationary phase for the column chromatography.

The thin-layer chromatography analyses were carried out with HPTLC pre-coated plates, silica gel 60 F 254 from E. Merck, Darmstadt.

The mixing ratios of the mobile phases for all the chromatography analyses are always stated in volume/volume.

The term "ether" means diethyl ether.

Example 1

2-Dimethylaminomethyl-1-pyridin-3-yl-indan-1-ol hydrochloride 37 ml of n-butyllithium solution (2.5 mol./l in hexane) were added dropwise at a temperature of from −35 to −40° C. to a solution of 8.8 ml of 3-bromopyridine in 130 ml of diethyl ether p.a. After a further 60 minutes at that temperature, 11.1 g of indan-1-one, dissolved in about 20 ml of diethyl ether p.a., were added dropwise, with continued cooling, and heating was carried out overnight to room temperature. Then about 30 ml of water were added at from 0 to 10° C., the phases were separated, the aqueous phase was extracted twice with tetrahydrofuran/diisopropyl ether, and the combined organic phases were dried over magnesium sulfate, filtered and concentrated. The resulting crude product (19.9 g) was chromatographed on silica gel with methanol/ethyl acetate (v/v=5:1). 7.0 g of pre-purified product were obtained, which was again chromatographed on silica gel with methanol/ethyl acetate (v/v=0:1 to 5:1). 3.54 g of the non-polar isomer of 2-dimethylaminomethyl-1-pyridin-3-yl-indan-1-ol were obtained and were dissolved in about 140 ml of acetone and converted into the corresponding hydrochloride with about 0.5 ml of water and about 3.7 ml of chlorotrimethylsilane; the hydrochloride washed with about 30 ml of absolute ethanol and dried in vacuo (about 50 mbar) (yield 2.64 g, melting point from 195° C. to 196° C. (decomposition)). In addition to 1.71 g of mixed fraction, 0.86 g of the polar isomer of 2-dimethylaminomethyl-1-pyridin-3-yl-indan-1-ol was obtained. The latter was dissolved in about 90 ml of acetone and converted into the corresponding hydrochloride with about 0.13 ml of water and about 0.90 ml of chlorotrimethylsilane (yield 0.76 g, melting point from 194° C. to 195° C. (decomposition)).

Examples 1 and 2 2-dimethylaminomethyl-1-pyridin-3-yl-indan-1-ol hydrochloride have hereby been described.

The compounds of Examples 8, 13 and 14 were obtained in an analogous manner.

Example 3

Dimethyl-(3-pyridin-3-yl-1H-inden-2-ylmethyl)-amine hydrochloride 2.6 ml of thionyl chloride were added dropwise, with the pronounced evolution of gas, to 2.17 g of 2-dimethylaminomethyl-1-pyridin-3-yl-indan-1-ol (mixture of the diastereoisomers), and the mixture was heated for 2.5 hours at 65° C., with stirring, and then concentrated in a water-jet pump. After cooling, first water and then 1 M sodium carbonate solution were added, and extraction was then carried out with tetrahydrofuran/ethyl acetate; the combined extracts were dried over magnesium sulfate, filtered and concentrated. The resulting crude product (1.4 g) was dissolved in about 17 ml of absolute ethanol and converted into the corresponding hydrochloride with water and chlorotrimethylsilane. The resulting solid was filtered off with suction, washed with a small amount of absolute ethanol and dried at 120° C. in vacuo (about 50 mbar). 1.74 g of dimethyl-(3-pyridin-3-yl-1H-inden-2-ylmethyl)-amine hydrochloride having a melting point of from 156° C. to 159° C. were obtained.

Example 3 dimethyl-(3-pyridin-3-yl-1H-inden-2-ylmethyl)-amine hydrochloride has hereby been described.

The compound of Example 9 was obtained in an analogous manner.

Example 4

Dimethyl-(1-pyridin-3-yl-indan-2-ylmethyl)-amine hydrochloride 1.25 g of dimethyl-(3-pyridin-3-yl-1H-inden-2-ylmethyl)-amine hydrochloride were dissolved in about 13 ml of methanol; 0.63 g of 10% palladium on animal charcoal was added, under nitrogen, and the mixture was stirred for 8 hours at room temperature under a hydrogen atmosphere of 2 bar. Filtration with suction was then carried out under nitrogen, followed by concentration. The residue was crystallised from about 12 ml of abs. ethanol. The filtrate was converted into the free base with 1 M sodium carbonate solution and dichloromethane, and the base was chromatographed on silica gel with methanol/dichloromethane (v/v=1:2), a mixed fraction and a pure fraction being obtained. The mixed fraction was again chromatographed on silica gel with methanol/dichloromethane (v/v=1:2). A total of 0.52 g of 2-dimethyl-(1-pyridin-3-yl-indan-2-ylmethyl)-amine was obtained and was dissolved in about 5 ml of acetone and converted into the corresponding hydrochloride with water and chlorotrimethylsilane (yield 0.36 g, melting point from 189° C. to 191° C.).

Example 4 dimethyl-(1-pyridin-3-yl-indan-2-ylmethyl)-amine hydrochloride has hereby been described.

The compound of Example 10 was obtained in an analogous manner.

Example 5

2-Dimethylaminomethyl-5-methoxy-1-pyridin-3-yl-indan-1-ol hydrochloride 47 ml of n-butyllithium solution (1.6 mol./l in n-hexane) were added dropwise at a temperature of from −30 to −35° C. to a solution of 7.3 ml of 3-bromopyridine in about 125 ml of diethyl ether p.a. After a further 20 minutes at that temperature, 11 g of 2-dimethylaminomethyl-5-methoxy-indan-1-one, dissolved in diethyl ether p.a., were added dropwise, with continued cooling, stirring was continued for 40 minutes at that temperature, and heating was carried out overnight to room temperature. Then 46 ml of water were added at from −10 to 0° C., the phases were separated, the aqueous phase was extracted with diethyl ether (monitoring by thin-layer chromatography), and the combined organic phases were washed with saturated sodium chloride solution and dried over magnesium sulfate, filtered and concentrated. The resulting crude product was chromatographed on silica gel with ethyl acetate/25% ammonia solution (v/v=98:2). 7.06 g of 2-dimethylaminomethyl-5-methoxy-1-pyridin-3-yl-indan-1-ol were obtained and were dissolved in about 125 ml of 2-butanone p.a. and converted into the corresponding hydrochloride with about 0.3 ml of water and about 4.2 ml of chlorotrimethylsilane, while cooling with ice; the hydrochloride was filtered off with suction with the exclusion of air and dried in vacuo (about 50 mbar) (yield 6.79 g, mixture of the two diastereoisomers).

Example 5 2-dimethylaminomethyl-5-methoxy-1-pyridin-3-yl-indan-1-ol hydrochloride has hereby been described.

The compounds of Examples 27, 28, 30, 31, 33 and 34 were obtained in an analogous manner.

Example 6

(6-Methoxy-3-pyridin-3-yl-1H-inden-2-ylmethyl)-dimethyl-amine hydrochloride

About 9 ml of 37% hydrochloric acid were added at room temperature to 0.837 g of 2-dimethylaminomethyl-5-methoxy-1-pyridin-3-yl-indan-1-ol hydrochloride (mixture of the diastereoisomers); the mixture was stirred overnight and then concentrated in vacuo at 70° C. The residue was taken up twice in dichloromethane and concentrated again. The oily brown residue was taken up in 40 ml of acetone and stirred, whereupon a crystalline solid formed. After further stirring for 2.5 days, filtration with suction was carried out with the exclusion of air, followed by washing twice with diethyl ether and drying under an oil-pump vacuum. 0.603 g of (6-methoxy-3-pyridin-3-yl-1H-inden-2-ylmethyl)-dimethyl-amine hydrochloride was obtained.

Example 6 6-methoxy-3-pyridin-3-yl-1H-inden-2-ylmethyl)-dimethyl-amine hydrochloride has hereby been described.

The compounds of Examples 15, 19, 23, 26, 29, 32 and 35 were obtained in an analogous manner.

Example 7

2-Dimethylaminomethyl-1-pyridin-3-yl-3H-inden-5-ol hydrochloride 0.84 g of 2-dimethylaminomethyl-5-methoxy-1-pyridin-3-yl-indan-1-ol hydrochloride (mixture of the diastereoisomers) was dissolved in about 13 ml of 33% hydrobromic acid in acetic acid and stirred for 3 hours under reflux at 100-110° C. The reaction mixture was concentrated in vacuo, rendered alkaline with 32% sodium hydroxide solution and extracted with ethyl acetate; the combined organic phases were dried over magnesium sulfate, stirred with activated carbon, filtered and concentrated. 0.62 g of 2-dimethylaminomethyl-1-pyridin-3-yl-3H-inden-5-ol was obtained and was dissolved in about 22 ml of 2-butanone/acetone (v/v=1:2) and converted into the corresponding hydrochloride with about 0.04 ml of water and about 0.58 ml of chlorotrimethylsilane, while cooling with ice; the hydrochloride was filtered off with suction, with the exclusion of air, washed with diisopropyl ether and dried in vacuo (about 50 mbar) (yield 0.631 g).

Example 7 2-dimethylaminomethyl-1-pyridin-3-yl-3H-inden-5-ol hydrochloride has hereby been described.

Example 11

6-Dimethylaminomethyl-5-pyridin-3-yl-6,7,8,9-tetrahydro-5H-benzocyclohepten-5-ol hydrochloride 50 ml of n-butyllithium solution (2.5 mol./l in n-hexane) were added dropwise at a temperature of from −35 to −40° C. to a solution of 12.0 ml of 3-bromopyridine in about 180 ml of diethyl ether p.a. After a further 60 minutes at that temperature, 14.2 g of 6-dimethylaminomethyl-6,7,8,9-tetrahydrobenzocyclohepten-5-one, dissolved in about 70 ml of diethyl ether p.a., were added dropwise, with continued cooling, and heating was carried out overnight to room temperature. Then about 30 ml of water were added at from 0 to 10° C., the phases were separated, the aqueous phase was extracted twice with tetrahydrofuran/diisopropyl ether, and the combined organic phases were dried over magnesium sulfate, filtered and concentrated. The resulting crude product (25.9 g) was chromatographed on silica gel with methanol/ethyl acetate (v/v=1:1). 17.9 g of product were obtained and were dissolved in absolute ethanol and converted into the corresponding hydrochloride with about 2.2 ml of water and about 15.5 ml of chlorotrimethylsilane; the hydrochloride was dried in vacuo (about 50 mbar) (yield 6.6 g, melting point 260° C. (decomposition)).

Example 11 6-dimethylaminomethyl-5-pyridin-3-yl-6,7,8,9-tetrahydro-5H-benzocyclohepten-5-ol hydrochloride has hereby been described.

Example 12

Dimethyl-(5-pyridin-3-yl-8,9-dihydro-7H-benzocyclohepten-6-ylmethyl)-amine hydrochloride 12 ml of thionyl chloride were added dropwise, with the pronounced evolution of gas, to 5.5 g of 6-dimethylaminomethyl-5-pyridin-3-yl-6,7,8,9-tetrahydro-5H-benzocyclohepten-5-ol hydrochloride, and the mixture was heated for 2 hours at 50° C., with stirring, and then concentrated in a water-jet pump. After cooling, first 2 N sodium hydroxide solution was added and then extraction was carried out with tetrahydrofuran/ethyl acetate; the combined extracts were dried over magnesium sulfate, filtered and concentrated. The resulting crude product (2.1 g) was chromatographed on silica gel with methanol/ethyl acetate (v/v=1:1). 2.01 g of pre-purified product were obtained, which was again chromatographed on silica gel with methanol/ethyl acetate/n-hexane (v/v/v=1:1:1). 1.25 g were obtained and were dissolved in about 10 ml of absolute ethanol/diisopropyl ether (v/v=1:1) and converted into the corresponding hydrochloride with about 0.16 ml of water and about 1.15 ml of chlorotrimethylsilane. The resulting solid was filtered off with suction, washed with a small amount of absolute ethanol and dried in vacuo (about 50 mbar). 0.449 g of dimethyl-(5-pyridin-3-yl-8,9-dihydro-7H-benzocyclohepten-6-ylmethyl)-amine hydrochloride having a melting point of from 259° C. to 260° C. was obtained.

Example 12 dimethyl-(5-pyridin-3-yl-8,9-dihydro-7H-benzocyclohepten-6-ylmethyl)-amine hydrochloride has hereby been described.

Example 16

Dimethyl-(1-oxo-5-pyridin-3-yl-2,3-dihydro-1H-1λ4-benzo[b]thiepin-4-ylmethyl)-amine hydrochloride 0.5 g of dimethyl-(5-pyridin-3-yl-2,3-dihydro-benzo[b]thiepin-4-ylmethyl)-amine hydrochloride was dissolved in 2.5 ml of glacial acetic acid; 0.29 ml of 35% hydrogen peroxide solution was added dropwise at room temperature, with stirring, and stirring was continued for 24 hours. The reaction mixture was covered with a layer of ethyl acetate, while cooling with ice, rendered alkaline with 32% sodium hydroxide solution and extracted three times with ethyl acetate; the combined organic phases were dried over magnesium sulfate, filtered and concentrated in vacuo. 0.35 g of crude product was obtained and was purified by means of preparative HPLC (Hypercarb 5 μm 120×4 mm, 0.5 ml/min., acetonitrile/water (v/v=70:30+0.1% diethylamine). After filtration through a MF-Millipore-MCE membrane (mixed cellulose esters; 0.45 μm), 0.102 g of dimethyl-(1-oxo-5-pyridin-3-yl-2,3-dihydro-1H-1λ4-benzo[b]thiepin-4-ylmethyl)-amine was obtained and was dissolved in 3 ml of 2-acetone p.a. and converted into the corresponding hydrochloride with about 0.003 ml of water and about 0.041 ml of chlorotrimethylsilane, while cooling with ice; the hydrochloride was dried in vacuo (about 50 mbar) (yield 0.1 g).

Example 16 dimethyl-(1-oxo-5-pyridin-3-yl-2,3-dihydro-1H-1λ4-benzo[b]thiepin-4-ylmethyl)-amine hydrochloride has hereby been described.

Example 17

4-Dimethylaminomethyl-1,1-dioxo-5-pyridin-3-yl-2,3,4,5-tetrahydro-1H-1λ6-benzo[b]thiepin-5-ol hydrochloride 0.5 g of 4-dimethylaminomethyl-5-pyridin-3-yl-2,3,4,5-tetrahydro-benzo[b]thiepin-5-ol hydrochloride was dissolved in 2.5 ml of glacial acetic acid; about 0.23 ml of 35% hydrogen peroxide solution was added dropwise at room temperature, with stirring, and stirring was continued for 24 hours. The reaction mixture was covered with a layer of ethyl acetate, while cooling with ice, rendered alkaline with 32% sodium hydroxide solution and extracted twice with ethyl acetate; the combined organic phases were washed with saturated sodium chloride solution, dried over magnesium sulfate, filtered and concentrated in vacuo. 0.38 g of crude product was obtained and was chromatographed on silica gel with ethyl acetate/25% ammonia solution (v/v=98:2). 0.15 g of a mixed fraction and 0.13 g of dimethyl-(1-oxo-5-pyridin-3-yl-2,3-dihydro-1H-1λ4-benzo[b]thiepin-4-ylmethyl)-amine were obtained. The latter was dissolved in 6 ml of 2-acetone p.a. and converted into the corresponding hydrochloride with about 0.004 ml of water and about 0.043 ml of chlorotrimethylsilane, while cooling with ice; the hydrochloride was dried in vacuo (about 50 mbar) (yield 0.09 g of white solid).

Example 17 4-dimethylaminomethyl-1,1-dioxo-5-pyridin-3-yl-2,3,4,5-tetrahydro-1H-1λ6-benzo[b]thiepin-5-ol hydrochloride has hereby been described.

Example 18

2-Dimethylaminomethyl-5-fluoro-1-pyridin-3-yl-indan-1-ol; hydrochloride

Step 1

2-Dimethylaminomethyl-5-fluoro-indan-1-one hydrochloride 2 g of 5-fluoro-indan-1-one were dissolved in 10.5 ml of acetonitrile; 1.84 ml of bisdimethylaminoethane were added, and 0.95 ml of acetyl chloride was added dropwise at from 0 to 10° C. Stirring was carried out for 3 hours at 50° C. and then for 18 hours at room temperature. The resulting precipitate was filtered off, washed once with acetonitrile/isopropyl ether (v/v=1:1) and twice with acetone and dried in vacuo (yield 2.9 g).

Step 2

2-Dimethylaminomethyl-5-fluoro-indan-1-one 2.8 g of 2-dimethylaminomethyl-5-fluoro-indan-1-one hydrochloride were dissolved in water; the solution was adjusted to pH 12 with 32% sodium hydroxide solution, while cooling with ice, and extracted three times with dichloromethane, and the combined organic phases were dried over magnesium sulfate, filtered and concentrated in vacuo.

Step 3

2-Dimethylaminomethyl-5-fluoro-1-pyridin-3-yl-indan-1-ol; hydrochloride

About 10 ml of n-butyllithium solution (1.6 mol./l in n-hexane) were added dropwise at a temperature of from −35 to −40° C. to a solution of 1.55 ml of 3-bromopyridine in about 28 ml of diethyl ether p.a. After a further 20 minutes at that temperature, 2.2 g of the product from step 2, dissolved in diethyl ether p.a., were added dropwise, with continued cooling, the mixture was stirred for 40 minutes at that temperature, and heating was carried out overnight to room temperature. 10.5 ml of water were then added at from −10 to 0° C., the phases were separated, the aqueous phase was extracted three times with diethyl ether (monitoring by thin-layer chromatography), and the combined organic phases were washed with saturated sodium chloride solution and dried over magnesium sulfate, filtered and concentrated. The resulting crude product was chromatographed on silica gel with ethyl acetate/25% ammonia solution (v/v=98:2). 1.5 g of 2-dimethylaminomethyl-5-fluoro-1-pyridin-3-yl-indan-1-ol were obtained and were dissolved in about 50 ml of acetone p.a. and converted into the corresponding hydrochloride with about 0.047 ml of water and about 0.665 ml of chlorotrimethylsilane, while cooling with ice; the hydrochloride was filtered off with suction, with the exclusion of air, and dried in vacuo (about 50 mbar) (yield 1.05 g, mixture of the two diastereoisomers).

Example 18 2-dimethylaminomethyl-5-fluoro-1-pyridin-3-yl-indan-1-ol hydrochloride has hereby been described.

Example 19

(6-Fluoro-3-pyridin-3-yl-1H-inden-2-ylmethyl)-dimethyl-amine hydrochloride

About 5.4 ml of 37% hydrochloric acid were added at room temperature to 0.5 g of 2-dimethylaminomethyl-5-fluoro-1-pyridin-3-yl-indan-1-ol hydrochloride (mixture of the diastereoisomers); stirring was carried out overnight, followed by concentration in vacuo. The residue was taken up twice in dichloromethane and concentrated again. The residue was taken up in 15 ml of acetone and stirred for 2 hours, whereupon a crystalline solid formed, which was filtered off with suction, with the exclusion of air, washed twice with diethyl ether and dried at 60° C. under an oil-pump vacuum. 0.39 g of (6-fluoro-3-pyridin-3-yl-1H-inden-2-ylmethyl)-dimethyl-amine hydrochloride was obtained.

Example 19 (6-fluoro-3-pyridin-3-yl-1H-inden-2-ylmethyl)-dimethyl-amine hydrochloride has hereby been described.

Example 20

2-Dimethylaminomethyl-1-pyridin-3-yl-5-trifluoromethoxy-indan-1-ol hydrochloride 5-Trifluoromethoxy-indan-1-one was prepared, departing from the literature (U.S. Pat. No. 6,159,996 A1, Dec. 12, 2000), as follows:

Step 1

3-(3-Trifluoromethoxy-phenyl)-propionic acid 0.69 g of 5% palladium on activated carbon was added, under a nitrogen atmosphere, to 15 g of 3-(trifluoromethoxy)-cinnamic acid in about 125 ml of ethyl acetate p.a., and hydrogenation was then carried out for 18 hours at room temperature under a hydrogen pressure of 2 bar. Filtration over kieselguhr was then carried out, followed by washing three times with ethyl acetate, and the combined filtrates were concentrated in vacuo at from 25 to 40° C. (yield 15.8 g).

Step 2

5-Trifluoromethoxy-indan-1-one

About 37 ml of trifluoromethanesulfonic acid were added at about 5° C., with stirring, to 12.4 g of the product from step 1, and stirring was then carried out for 18 hours at room temperature. Crushed ice was then added, followed by extraction with diethyl ether. The combined organic phases were washed with saturated sodium hydrogen carbonate solution, water and saturated sodium chloride solution, and dried over magnesium sulfate, filtered and concentrated in vacuo at from 25 to 40° C. (yield 10.1 g).

Step 3

2-Dimethylaminomethyl-5-trifluoromethoxy-indan-1-one hydrochloride 6.4 ml of bis-(dimethylamino)-methane were added to a solution of 10.1 g of the product from step 2 in 37 ml of acetonitrile; 3.3 ml of acetic acid chloride were added dropwise at from 0 to 10° C., a further 25 ml of acetonitrile were added, and stirring was carried out for 3 hours at 50° C. and then for 18 hours at room temperature. The resulting solid was filtered off with suction, washed twice with diethyl ether and dried in vacuo (yield 12.4 g).

Step 4

2-Dimethylaminomethyl-5-trifluoromethoxy-indan-1-one 14 g of the product from step 3 were dissolved in water; the solution was adjusted to pH 12 with 32% sodium hydroxide solution, while cooling with ice, and extracted three times with dichloromethane, and the combined organic phases were dried over magnesium sulfate, filtered and concentrated in vacuo.

Step 5

2-Dimethylaminomethyl-1-pyridin-3-yl-5-trifluoromethoxy-indan-1-ol 39 ml of n-butyllithium solution (1.6 mol./l in n-hexane) were added dropwise at a temperature of from −35 to −40° C. to a solution of 6.0 ml of 3-bromopyridine in about 108 ml of diethyl ether p.a. After a further 20 minutes at that temperature, 11.3 g of the product from step 4, dissolved in diethyl ether p.a., were added dropwise, with continued cooling, the mixture was stirred for 40 minutes at that temperature, and heating was carried out overnight to room temperature. 41 ml of water were then added at from −10 to 0° C., the phases were separated, the aqueous phase was extracted three times with diethyl ether (monitoring by thin-layer chromatography), and the combined organic phases were washed with saturated sodium chloride solution and dried over magnesium sulfate, filtered and concentrated. The resulting crude product was chromatographed on silica gel with ethyl acetate/25% ammonia solution (v/v=98:2). 3.4 g of the non-polar diastereoisomer of 2-dimethylaminomethyl-1-pyridin-3-yl-5-trifluoromethoxy-indan-1-ol and 8.7 g of a mixture of the non-polar and of the polar diastereoisomer of 2-dimethylamino-methyl-1-pyridin-3-yl-5-trifluoromethoxy-indan-1-ol, contaminated with acetic acid amide, were obtained. The contaminated diastereoisomeric mixture was taken up in 50 ml of diethyl ether, stirred for 20 minutes at 40° C. and stirred further while cooling with ice, and the resulting precipitate was filtered off with suction. The mother liquor was dissolved in 15 ml of diethyl ether and the resulting precipitate was filtered off with suction. The mother liquor was dissolved in 20 ml of diethyl ether/n-hexane (v/v=1:1), filtered over a MF-Millipore-MCE membrane (mixed cellulose esters; 0.45 μm) and concentrated in vacuo. 6.3 g of pure diastereoisomeric mixture of 2-dimethylamino-methyl-1-pyridin-3-yl-5-trifluoromethoxy-indan-1-ol were obtained and were dissolved in about 80 ml of acetone p.a. and converted into the corresponding hydrochloride with about 0.322 ml of water and about 4.54 ml of chlorotrimethylsilane, in each case in four portions, while cooling with ice; the hydrochloride was dried in vacuo (about 50 mbar) (yield 6.6 g of 2-dimethylamino-methyl-1-pyridin-3-yl-5-trifluoromethoxy-indan-1-ol hydrochloride (mixture of the diastereoisomers)).

Example 20 2-dimethylaminomethyl-1-pyridin-3-yl-5-trifluoromethoxy-indan-1-ol hydrochloride has hereby been described.

Example 21

Dimethyl-(3-pyridin-3-yl-6-trifluoromethoxy-1H-inden-2-ylmethyl)-amine hydrochloride About 10.8 ml of 37% hydrochloric acid were added at room temperature to 1.2 g of 2-dimethylaminomethyl-1-pyridin-3-yl-5-trifluoromethoxy-indan-1-ol hydrochloride (mixture of the diastereoisomers), and stirring was carried out overnight; 15 ml of acetone p.a. were added, and stirring was carried out for 2 hours. An oily, semi-crystalline precipitate formed, from which the supernatant was separated off. The residue was taken up in about 40 ml of acetone p.a. and stirred, whereupon fine crystals formed, which were filtered off with suction, with the exclusion of air, washed twice with diethyl ether and dried under an oil-pump vacuum at from 25 to 60° C. 1.17 g of dimethyl-(3-pyridin-3-yl-6-trifluoromethoxy-1H-inden-2-ylmethyl)-amine hydrochloride were obtained.

Example 21 dimethyl-(3-pyridin-3-yl-6-trifluoromethoxy-1H-inden-2-ylmethyl)-amine hydrochloride has hereby been described.

Example 22

2-Dimethylaminomethyl-1-pyridin-3-yl-5-trifluoromethyl-indan-1-ol hydrochloride The title compound was obtained by replacing the indanone in Example 18 by 5-trifluoromethyl-indan-1-one and using paraformaldehyde and dimethylammonium chloride in Example 18, step 1, and by using the processes described in Example 18, steps 2 to 3.

5-Trifluoromethyl-indan-1-one was obtained by replacing 3-(trifluoromethoxy)-cinnamic acid in Example 20, step 1, by 3-(trifluoromethyl)-cinnamic acid and using the processes described in Example 20, steps 1 to 2, and then separating off 7-trifluoromethyl-indan-1-one by column chromatography.

Example 22 2-dimethylaminomethyl-1-pyridin-3-yl-5-trifluoromethyl-indan-1-ol hydrochloride has hereby been described.

Example 24

4-Dimethylaminomethyl-5-pyridin-3-yl-2,3,4,5-tetrahydro-benzo[b]oxepin-5-ol hydrochloride The title compound was obtained by replacing the indanone in Example 18 by 3,4-dihydro-2H-benzo[b]oxepin-5-one.

3,4-Dihydro-2H-benzo[b]oxepin-5-one was advantageously obtained, departing from the literature (A. Orita, J. Yaruva, J. Otera *Angew. Chem.* 1999, 111, 2397), by reaction of phenoxybutyric acid with polyphosphoric acid.

Examples 24 and 25 4-dimethylaminomethyl-5-pyridin-3-yl-2,3,4,5-tetrahydro-benzo[b]oxepin-5-ol hydrochloride have hereby been described.

Example 36

2-Dimethylaminomethyl-5-methoxy-1-pyridin-3-yl-1,2,3,4-tetrahydro-naphthalen-1-ol hydrochloride

Step 1

2-Dimethylaminomethyl-5-methoxy-3,4-dihydro-2H-naphthalen-1-one hydrochloride 3.9 ml of bis-(dimethylamino)-methane were added to a solution of 5 g of 5-methoxy-1-tetralone in 12 ml of acetonitrile; 2.0 ml of acetic acid chloride were added dropwise at from 0 to 10° C., a further 10 ml of acetonitrile were added, and stirring was carried out for 3 hours at 50° C. and then for 18 hours at room temperature. The resulting solid was filtered off with suction, washed twice with diethyl ether and dried in vacuo (yield 6.4 g).

Step 2

2-Dimethylaminomethyl-5-methoxy-3,4-dihydro-2H-naphthalen-1-one 16 g of the product from step 1 were dissolved in water; the solution was adjusted to pH 12 with 32% sodium hydroxide solution, while cooling with ice, and extracted three times with dichloromethane, and the combined organic phases were dried over magnesium sulfate, filtered and concentrated in vacuo.

Step 3

2-Dimethylaminomethyl-5-methoxy-1-pyridin-3-yl-1,2,3,4-tetrahydro-naphthalen-1-ol hydrochloride About 65 ml of n-butyllithium solution (1.6 mol./l in n-hexane) were added dropwise at a temperature of from −35 to −40° C. to a solution of 10.0 ml of 3-bromopyridine in about 180 ml of diethyl ether p.a. After a further 20 minutes at that temperature, 16 g of the product from step 2, dissolved in diethyl ether p.a., were added dropwise, with continued cooling, the mixture was stirred for 40 minutes at that temperature, and heating was carried out overnight to room temperature. 68 ml of water were then added at from −10 to 0° C., the phases were separated, the aqueous phase was extracted twice with diethyl ether (monitoring by thin-layer chromatography), and the combined organic phases were washed with saturated sodium chloride solution and dried over magnesium sulfate, filtered and concentrated.

The resulting crude product was chromatographed on silica gel first with diethyl ether/25% ammonia solution (v/v=98:2) and then with diethyl ether/methanol/25% ammonia solution (v/v/v=93:5:2). 2.59 g of the non-polar isomer of 2-dimethylaminomethyl-5-methoxy-1-pyridin-3-yl-1,2,3,4-tetrahydro-naphthalen-1-ol were obtained and were dissolved in about 100 ml of acetone and converted into the corresponding hydrochloride with about 0.075 ml of water and about 1.05 ml of chlorotrimethylsilane. The hydrochloride was filtered off with suction, with the exclusion of air, washed twice with diethyl ether and dried in vacuo at room temperature and then in a desiccator under an oil-pump vacuum over Sicacide (sulfuric acid on inert siliceous carrier material) (yield 2.4 g).

6.9 g of the polar isomer of 2-dimethylaminomethyl-5-methoxy-1-pyridin-3-yl-1,2,3,4-tetrahydro-naphthalen-1-ol were also obtained and were dissolved in about 200 ml of acetone and converted into the corresponding hydrochloride by addition of about 0.25 ml of water and about 3.5 ml of chlorotrimethylsilane, in each case in three portions, followed by stirring for 1.5 hours at room temperature. The hydrochloride was filtered off with suction, with the exclusion of air, washed twice with diethyl ether and dried in vacuo at room temperature and then in a desiccator under an oil-pump vacuum over Sicacide (yield 7.9 g).

Examples 36 and 37 2-dimethylaminomethyl-5-methoxy-1-pyridin-3-yl-1,2,3,4-tetrahydro-naphthalen-1-ol hydrochloride have hereby been described.

Example 38

(5-Methoxy-1-pyridin-3-yl-3,4-dihydro-naphthalen-2-ylmethyl)-dimethyl-amine hydrochloride About 12 ml of 37% hydrochloric acid were added, at room temperature, to 1.2 g of the polar isomer of 2-dimethylaminomethyl-5-methoxy-1-pyridin-3-yl-1,2,3,4-tetrahydro-naphthalen-1-ol; stirring was carried out overnight at room temperature and for 2 hours at 50° C., followed by concentration in vacuo at 70° C. The residue was taken up twice in dichloromethane and concentrated again. The oily brown residue was taken up in 40 ml of acetone p.a. and stirred, whereupon a crystalline solid formed. It was filtered off with suction, with the exclusion of air, washed twice with diethyl ether and dried under an oil-pump vacuum.

37% hydrochloric acid was again added to the solid, and stirring was carried out overnight, followed by concentration in vacuo at 70° C. The residue was taken up twice in dichloromethane and concentrated again. The beige-coloured solid was taken up in 40 ml of acetone p.a. and stirred for 2 hours, filtered off with suction, with the exclusion of air, and dried under an oil-pump vacuum at from 25 to 60° C. (yield 0.68 g).

Example 38 (5-methoxy-1-pyridin-3-yl-3,4-dihydro-naphthalen-2-ylmethyl)-dimethyl-amine hydrochloride has hereby been described.

Example 39

6-Dimethylaminomethyl-5-pyridin-3-yl-7,8-dihydro-naphthalen-1-ol hydrochloride 1.25 g of the polar isomer of 2-dimethylaminomethyl-5-methoxy-1-pyridin-3-yl-1,2,3,4-tetrahydro-naphthalen-1-ol were dissolved in about 16 ml of 33% hydrobromic acid in acetic acid, and stirring was carried out for 5 hours under reflux and then for 18 hours without heating. The reaction mixture was concentrated in vacuo, the residue was taken up in ice-water, and the aqueous phase washed with diethyl ether. The aqueous phase was rendered alkaline with 32% sodium hydroxide solution and extracted with ethyl acetate, and the combined organic phases were dried over magnesium sulfate, filtered and concentrated.

The resulting crude product was chromatographed on silica gel with ethyl acetate/25% ammonia solution (v/v=98:2). 0.86 g of 6-dimethylaminomethyl-5-pyridin-3-yl-7,8-dihydro-naphthalen-1-ol was obtained and was dissolved in about 20 ml of acetone p.a. and converted into the corresponding hydrochloride with about 0.027 ml of water and about 0.380 ml of chlorotrimethylsilane, while cooling with ice; the hydrochloride was filtered off with suction, with the exclusion of air, and dried in vacuo (about 50 mbar) (yield 0.67 g).

Example 39 6-dimethylaminomethyl-5-pyridin-3-yl-7,8-dihydro-naphthalen-1-ol hydrochloride has hereby been described.

Pharmacological Studies a) Methods of Determining Affinity for the Human μ-Opiate Receptor and the Inhibition of 5-HT and NA Reuptake Study of Affinity for the Human μ-Opiate Receptor The receptor affinity for the human μ-opiate receptor was determined in a homogeneous batch on microtitre plates. To that end, serial dilutions of the substances to be tested were incubated for 90 minutes at room temperature with a receptor membrane preparation (15-40 μg of protein/250 μl of incubation batch) of CHO-K1 cells, which express the human μ-opiate receptor (RB-HOM receptor membrane preparation from Perkin Elmer, Zaventem, Belgium), in the presence of 1 nmol./l of the radioactive ligand [$^3$H]-naloxone (NET719, Perkin Elmer, Zaventem, Belgium) and 1 mg of WGA-SPA beads (wheatgerm agglutinin SPA beads from Amersham/Pharmacia, Freiburg, Germany) in a total volume of 250 μl. The incubation buffer used was 50 mmol./l of Tris-HCl supplemented with 50 μM $MgCl_2$ and 0.05% bovine serum albumin. In order to determine non-specific binding, 100 μmol./l of naloxone were additionally added. When the ninety-minute incubation time was complete, the microtitre plates were centrifuged off for 20 minutes at 1000 g and the radioactivity was measured in a β-counter (Microbeta-Trilux, PerkinElmer, Freiburg, Germany). The percentage displacement of the radioactive ligand from its binding to the human μ-opiate receptor at a concentration of the test substances of 1 μmol./l was determined and stated as the percentage inhibition of specific binding. Starting from the percentage displacement, $IC_{50}$ inhibitory concentrations, which effect 50% displacement of the radioactive ligand, were calculated by means of different concentrations of the test substances. $K_i$ values for the test substances were obtained by conversion by means of the Cheng-Prusoff equation (Cheng and Prusoff 1973).

Studies of the Inhibition of 5-HT and NA Reuptake

In order to be able to carry out these in vitro studies, synaptosomes were freshly isolated from areas of rat brain. A so-called "$P_2$" fraction was used in each case, which was prepared exactly according to the procedure of Gray, E. G. and Whittaker, V. P. (1962, J. Anat. 76, 79-88). For NA reuptake, these vesicular particles were isolated from the hypothalamus of male rat brains, and for 5HT reuptake, they were isolated from the medulla+pons region.

The following characteristic data were determined for the NA and 5-HT reuptake:

NA uptake: Km=0.32±0.11 μM

5-HT uptake: Km=0.084±0.011 μM (in each case N=4, i.e. mean values±SEM from 4 independent test series which were carried out in triplicate parallel tests).

A detailed description of the method can be found in the publication of Frink, M. Ch., Hennies, H. H., Englberger, W. et al. (1996, Arzneim.-Forsch./Drug Res. 46(III) 11, 1029-1036) (the batch can also be carried out on microtitre plates (250 μl/well) at room temperature).

Evaluations:

In addition to % inhibitions at fixed concentrations of test substance (e.g. $1 \times 10^{-6}$ M or $1 \times 10^{-5}$ M in the batch), dose dependencies were also checked. $IC_{50}$ values were obtained thereby which can be converted into inhibitor constants ($K_i$) according to the "Cheng-Prusoff equation" (Cheng, Y. C. and Prusoff, W. H., 1973, Biochem. Pharmacol. 22, 3099-3108). The $IC_{50}$ values were obtained with the aid of the "Figure P" computer program (Version 6.0, Biosoft, Cambridge, England). Km values were calculated according to Lineweaver, H. and Burk, D. (1934, J. Am. Chem. Soc. 56, 658-666). The "Ligand" computer program (Version 4, Biosoft, England) was used to show $K_D$ values.

For the compounds according to the invention, a marked affinity for the μ-opiate receptor and/or marked inhibition of serotonin and/or noradrenaline reuptake was measured. The results of examples and for the reference substances venlafaxin and duloxetin are shown in the following table.

TABLE 1

| Compound according to Example number | μ-Opioid receptor affinity (% inhibition at 1 μmol./l or Ki (μmol./l)) | Inhibition of 5-HT reuptake (% inhibition at 10 μmol./l or Ki (μmol./l)) | Inhibition of NA reuptake (% inhibition at 10 μmol./l or Ki (μmol./l)) |
|---|---|---|---|
| 1 | 1% | 63% | 33% |
| 2 | 60% | 89% | 43% |
| 3 | 0.24 μmol./l | 0.013 μmol./l | 30% |
| 4 | 31% | 86% | 46% |
| 5 | 49% | 0.17 μmol./l | 29% |
| 6 | 0.15 μmol./l | 0.028 μmol./l | 31% |
| 7 | 0.38 μmol./l | 0.025 μmol./l | 59% |
| 9 | 0.56 μmol./l | 56% | 26% |
| 11 | 20% | 0.028 μmol./l | 39% |
| 12 | 0.38 μmol./l | 0.12 μmol./l | 20% |
| 13 | −23% | 41% | 45% |
| 14 | −14% | 44% | 54% |
| 15 | 0.32 μmol./l | 60% | 36% |
| 16 | 0.21 μmol./l | 35% | −2% |
| 17 | −13% | 57% | 19% |
| 18 | −6% | 56% | 29% |
| 19 | 0.29 μmol./l | 0.043 μmol./l | 31% |
| 20 | −19% | 71% | 38% |
| 21 | 5% | 0.43 μmol./l | 14% |
| 22 | 2% | 61% | 17% |
| 23 | −8% | 47% | 6% |
| 24 | 45% | 12% | 9% |
| 26 | 37% | 50% | 9% |
| 31 | — | −4% | 48% |
| 36 | −14% | 33% | 49% |
| 37 | 8% | 19% | 57% |
| 38 | 0.46 μmol./l | 0.37 μmol./l | 34% |
| 39 | 0.02 μmol./l | 0.25 μmol./l | 50% |
| Venlafaxin | −1% | 0.062 μmol./l | 0.45 μmol./l |
| Duloxetin | −10% | 0.0046 μmol./l | 0.057 μmol./l | a) Studies of Analgesic Activity in the Formalin Test on the Mouse and the Rat

The formalin test (Dubuisson, D. and Dennis, S. G., 1977, Pain, 4, 161-174) represents a model for acute and chronic pain. By means of a single formalin injection into the dorsal side of a rear paw, a biphase nociceptive reaction was induced in freely mobile test animals; the reaction was assessed by observing three behaviour patterns which are clearly distinguishable from one another. The reaction is two-phase: phase 1=immediate reaction (duration up to 10 minutes; shaking of the paw, licking), phase 2=late reaction (after a rest phase; likewise shaking of the paw, licking; duration up to 60 minutes). The first phase reflects a direct stimulation of the peripheral nocisensors with a high spinal nociceptive input or glutamate release (acute pain phase); the second phase reflects a spinal and peripheral hypersensitisation (chronic pain phase). In the studies presented here, the chronic pain component (phase 2) was evaluated.

Formalin Test in the Rat:

Formalin was administered subcutaneously in a volume of 50 µl and a concentration of 5% into the dorsal side of the right rear paw of each animal. The specific behavioural changes, such as lifting and shaking of the paw, weight shifting of the animal and biting and licking reactions, were observed and recorded over an observation period of from 21 to 27 minutes after the formalin injection. The various behaviours were combined to give the so-called pain rate (PR) which, based on 3-minute intervals, represents the calculation of a mean nociceptive reaction. The PR was calculated on the basis of a numerical weighting (=in each case factor 1, 2, 3) of the observed behaviours (corresponding to behaviour score 1, 2, 3) and was calculated using the following formula:

$PR = [(T_0 \times 0) + (T_1 \times 1) + (T_2 \times 2) + (T_3 \times 3)]/180$, where $T_0$, $T_1$, $T_2$ and $T_3$ correspond to the time, in seconds, at which the animal exhibited behaviour 0, 1, 2 or 3. The size of the group was 10 animals (n=10).

Formalin Test in the Mouse:

Formalin was administered subcutaneously in a volume of 20 µl and a concentration of 1% into the dorsal side of the right rear paw of each animal. The specific behavioural changes, such as lifting and shaking of the paw (score 3), were observed and recorded over an observation period of from 21 to 24 minutes after the formalin injection. The size of the group was 10 animals (n=10).

On the basis of the PR calculations, the activity of the substance was determined in percent as the change relative to a control. The $ED_{50}$ was determined by means of regression analysis.

An inhibition of the nociceptive behaviour was observed for the compounds according to the invention and also for the reference substances venlafaxin and duloxetin. The results are shown in the following table.

TABLE 2

| Compound according to Example number | Species | Dose (mg/kg i.v.) | Inhibition of the nociceptive behaviour versus control (% inhibition) | Inhibition of the nociceptive behaviour versus control, $ED_{50}$ value (mg/kg i.v.) |
|---|---|---|---|---|
| 2 | rat | 46.4 | −80.6 | — |
| 3 | mouse | — | — | 3.32 |
| 4 | rat | 4.64 | −61.60 | |
| 5 | rat | 21.5 | −43.0 | |
| 6 | mouse | — | — | 1.64 |
| 7 | rat | — | — | 2.93 |
| 8 | rat | 46.4 | −65.8 | — |
| 9 | rat | 10 | −97.0 | |
| 12 | mouse | 14.7 | −45.8 | — |
| 13 | rat | 21.5 | −53.6 | — |
| 14 | rat | 21.5 | −53.2 | — |
| 15 | rat | 10.0 | −70.7 | — |
| Venlafaxin | mouse | — | — | 2.60 |
| Duloxetin | rat | — | — | 1.43 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A saturated or unsaturated 3-pyridyl-benzocycloalkyl-methyl-amine compound corresponding to formula I

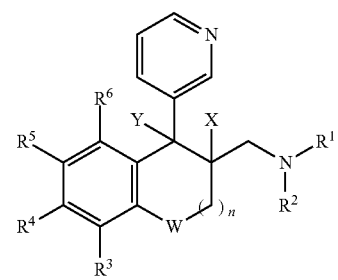

wherein

W is $CH_2$, and n=from 0 to 3, $R^1$ and $R^2$, independently of one another, are selected from H, $C_1$-$C_{10}$-alkyl, $C_2$-$C_{10}$-alkenyl or $C_3$-$C_{10}$-alkynyl, in each case branched or unbranched, mono- or poly-substituted or unsubstituted; $C_3$-$C_7$-cycloalkyl, saturated or unsaturated, mono- or poly-substituted or unsubstituted, or a corresponding heterocycle in which a carbon atom in the ring has been replaced by S, O or $NR^{3'}$, where $R^{3'}$ is selected from H, $C_1$-$C_{10}$-alkyl, $C_2$-$C_{10}$-alkenyl or $C_2$-$C_{10}$-alkynyl, in each case branched or unbranched, mono- or poly-substituted or unsubstituted;

alkylaryl, saturated or unsaturated, mono- or poly-substituted or unsubstituted; aryl, mono- or poly-substituted or unsubstituted;

or $R^1$ and $R^2$ together form a $C_3$-$C_7$-cycloalkyl, saturated or unsaturated, mono- or poly-substituted or unsubstituted, or a corresponding heterocycle in which a carbon atom in the ring has been replaced by S, O or $NR^{4'}$, where $R^{4'}$ is selected from H, $C_1$-$C_{10}$-alkyl, $C_2$-$C_{10}$-alkenyl or $C_3$-$C_{10}$-alkynyl, in each case branched or unbranched, mono- or poly-substituted or unsubstituted;

and $R^3$ to $R^6$, independently of one another, are selected from H or any radicals selected from the group consisting of F, Cl, Br, I, CN, $CF_3$, $OCF_3$, $NO_2$, $C_1$-$C_{10}$-alkyl, $C_2$-$C_{10}$-alkenyl and $C_3$-$C_{10}$-alkynyl, in each case branched or unbranched, mono- or poly-substituted or unsubstituted; $C_3$-$C_7$-cycloalkyl, saturated or unsaturated, mono- or poly-substituted or unsubstituted, or a corresponding heterocycle in which a carbon atom in the ring has been replaced by S, O or $NR^{5'}$, where $R^{5'}$ is selected from H, $C_1$-$C_{10}$-alkyl, $C_2$-$C_{10}$-alkenyl or $C_2$-$C_{10}$-alkynyl, in each case branched or unbranched, mono- or poly-substituted or unsubstituted;

$OR^{6'}$, $OC(O)R^{6'}$, $OC(S)R^{6'}$, $C(O)R^{6'}$, $C(O)OR^{6'}$, $C(S)R^{6'}$, $C(S)OR^{6'}$, $SR^{6'}$, $S(O)R^{6'}$ or $S(O_2)R^{6'}$, where $R^{6'}$ is selected from H, $C_1$-$C_{10}$-alkyl, $C_2$-$C_{10}$-alkenyl or $C_2$-$C_{10}$-alkynyl, in each case branched or unbranched, mono- or poly-substituted or unsubstituted; $C_3$-$C_7$-cycloalkyl, saturated or unsaturated, mono- or poly-substituted or unsubstituted, or a corresponding heterocycle in which a carbon atom in the ring has been replaced by S, O or $NR^7$, where $R^7$ is selected from H, $C_1$-$C_{10}$-alkyl, $C_2$-$C_{10}$-alkenyl or $C_3$-$C_{10}$-alkynyl, in each case branched or unbranched, mono- or poly-substituted or unsubstituted;

alkylaryl, saturated or unsaturated, mono- or poly-substituted or unsubstituted; aryl or 5- or 6-membered heteroaryl aromatic rings containing 1 or 2 heteroatoms selected from the group consisting of O, N and S, in each case mono- or poly-substituted or unsubstituted;

$NR^8R^9$, $C(O)NR^8R^9$ or $S(O_2)NR^8R^9$ wherein $R^8$ and $R^9$, independently of one another, are selected from H, $C_1$-$C_{18}$-alkyl, $C_2$-$C_{18}$-alkenyl or $C_3$-$C_{18}$-alkynyl, in each case branched or unbranched, mono- or poly-substituted or unsubstituted; $C_3$-$C_7$-cycloalkyl, saturated or unsaturated, mono- or poly-substituted or unsubstituted, or a corresponding heterocycle in which a carbon atom in the ring has been replaced by S, O or $NR^{10}$, where $R^{10}$ is selected from H, $C_1$-$C_{10}$-alkyl, $C_2$-$C_{10}$-alkenyl or $C_3$-$C_{10}$-alkynyl, in each case branched or unbranched, mono- or poly-substituted or unsubstituted;

alkylaryl, saturated or unsaturated, mono- or poly-substituted or unsubstituted; aryl or 5- or 6-membered heteroaryl aromatic rings containing 1 or 2 heteroatoms selected from the group consisting of O, N and S, in each case mono- or poly-substituted or unsubstituted;

or $R^8$ and $R^9$ together form a $C_3$-$C_7$-cycloalkyl, saturated or unsaturated, mono- or poly-substituted or unsubstituted, or a corresponding heterocycle in which a carbon atom in the ring has been replaced by S, O or $NR^{10}$, where $R^{10}$ is selected from H, $C_1$-$C_{10}$-alkyl, $C_2$-$C_{10}$-alkenyl or $C_3$-$C_{10}$-alkynyl, in each case branched or unbranched, mono- or poly-substituted or unsubstituted;

alkylaryl, aryl or 5- or 6-membered heteroaryl aromatic rings containing 1 or 2 heteroatoms selected from the group consisting of O, N and S, in each case mono- or poly-substituted or unsubstituted, and Y is selected from H and OH when X is simultaneously H, or X and Y together form a bond, wherein mono- or poly-substituted means the replacement of one or more hydrogens with one or more substituents selected from the group consisting of F, Cl, Br, I, $NH_2$, SH, OH, and $OCH_3$;

optionally in the form of an isolated enantiomer or isolated diastereomer or an optionally racemic mixture of stereoisomers;

or a salt thereof with physiologically acceptable acid.

2. The compound of claim 1, wherein said compound is present in the form of a salt with physiologically acceptable acid.

3. The compound of claim 1, wherein said compound is present in the form of an isolated enantiomer or isolated diastereoisomer.

4. The compound of claim 1, wherein said compound is present in the form of a mixture of stereoisomers.

5. The compound of claim 4, wherein said compound is present in the form of a racemic mixture.

6. The compound of claim 1, wherein n<3.

7. The compound of claim 1, wherein $W=CH_2$, n<3, $R^1$ and $R^2$ each=methyl, and $R^5$ and $R^6$ each=H.

8. The compound of claim 1, wherein said compound is selected from the group consisting of:

2-dimethylaminomethyl-1-pyridin-3-yl-indan-1-ol and the corresponding hydrochloride;

dimethyl-(3-pyridin-3-yl-1H-inden-2-ylmethyl)-amine and the corresponding hydrochloride;

dimethyl-(1-pyridin-3-yl-indan-2-ylmethyl)-amine and the corresponding hydrochloride;

2-dimethylaminomethyl-5-methoxy-1-pyridin-3-yl-indan-1-ol and the corresponding hydrochloride;

(6-methoxy-3-pyridin-3-yl-1H-inden-2-ylmethyl)-dimethyl-amine and the corresponding hydrochloride;

2-dimethylaminomethyl-1-pyridin-3-yl-3H-inden-5-ol and the corresponding hydrochloride;

2-dimethylaminomethyl-1-pyridin-3-yl-1,2,3,4-tetrahydro-naphthalen-1-ol and the corresponding hydrochloride;

dimethyl-(1-pyridin-3-yl-3,4-dihydro-naphthalen-2-ylmethyl)-amine and the corresponding hydrochloride;

dimethyl-(1-pyridin-3-yl-1,2,3,4-tetrahydro-naphthalen-2-ylmethyl)-amine and the corresponding hydrochloride;

6-dimethylaminomethyl-5-pyridin-3-yl-6,7,8,9-tetrahydro-5H-benzocyclohepten-5-ol and the corresponding hydrochloride;

dimethyl-(5-pyridin-3-yl-8,9-dihydro-7H-benzocyclohepten-6-ylmethyl)-amine and the corresponding hydrochloride;

2-dimethylaminomethyl-5-fluoro-1-pyridin-3-yl-indan-1-ol and the corresponding hydrochloride;

(6-fluoro-3-pyridin-3-yl-1H-inden-2-ylmethyl)-dimethyl-amine and the corresponding hydrochloride;

2-dimethylaminomethyl-1-pyridin-3-yl-5-trifluoromethoxy-indan-1-ol and the corresponding hydrochloride;

dimethyl-(3-pyridin-3-yl-6-trifluoromethoxy-1H-inden-2-ylmethyl)-amine and the corresponding hydrochloride;

2-dimethylaminomethyl-1-pyridin-3-yl-5-trifluoromethyl-indan-1-ol and the corresponding hydrochloride;

dimethyl-(3-pyridin-3-yl-6-trifluoromethyl-1H-inden-2-ylmethyl)-amine and the corresponding hydrochloride;

2-dimethylaminomethyl-6-methoxy-1-pyridin-3-yl-indan-1-ol and the corresponding hydrochloride;

(5-methoxy-3-pyridin-3-yl-1H-inden-2-ylmethyl)-dimethyl-amine and the corresponding hydrochloride;

2-di methylaminomethyl-5-methoxy-1-pyridin-3-yl-1,2,3,4-tetrahydro-naphthalen-1-ol and the corresponding hydrochloride;

(5-methoxy-1-pyridin-3-yl-3,4-dihydro-naphthalen-2-ylmethyl)-dimethyl-amine and the corresponding hydrochloride, and 6-dimethylaminomethyl-5-pyridin-3-yl-7,8-dihydro-naphthalen-1-ol and the corresponding hydrochloride.

9. The compound of claim 1, wherein said compound is selected from the group consisting of:

dimethyl-(3-pyridin-3-yl-1H-inden-2-ylmethyl)-amine and the corresponding hydrochloride;

(6-methoxy-3-pyridin-3-yl-1H-inden-2-ylmethyl)-dimethyl-amine and the corresponding hydrochloride;

2-dimethylaminomethyl-1-pyridin-3-yl-3H-inden-5-ol and the corresponding hydrochloride;

6-dimethylaminomethyl-5-pyridin-3-yl-6,7,8,9-tetrahydro-5H-benzocyclohepten-5-ol and the corresponding hydrochloride;

dimethyl-(5-pyridin-3-yl-8,9-dihydro-7H-benzocyclohepten-6-ylmethyl)-amine and the corresponding hydrochloride;

(6-fluoro-3-pyridin-3-yl-1H-inden-2-ylmethyl)-dimethyl-amine and the corresponding hydrochloride;

dimethyl-(3-pyridin-3-yl-6-trifluoromethoxy-1H-inden-2-ylmethyl)-amine and the corresponding hydrochloride;

(5-methoxy-1-pyridin-3-yl-3,4-dihydro-naphthalen-2-ylmethyl)-dimethyl-amine and the corresponding hydrochloride, and 6-dimethylaminomethyl-5-pyridin-3-yl-7,8-dihydro-naphthalen-1-ol and the corresponding hydrochloride.

10. A process for preparing a saturated or unsaturated 3-pyridyl-benzocycloalkylmethyl-amine compound corresponding to formula I

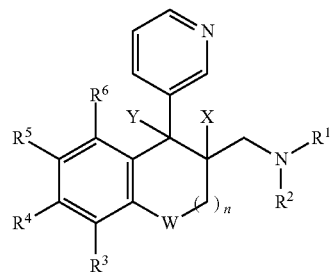

I wherein

W is $CH_2$, and n=from 0 to 3, $R^1$ and $R^2$, independently of one another, are selected from H, $C_1$-$C_{10}$-alkyl, $C_2$-$C_{10}$-alkenyl or $C_3$-$C_{10}$-alkynyl, in each case branched or unbranched, mono- or poly-substituted or unsubstituted; $C_3$-$C_7$-cycloalkyl, saturated or unsaturated, mono- or poly-substituted or unsubstituted, or a corresponding heterocycle in which a carbon atom in the ring has been replaced by S, O or $NR^{3'}$, where $R^{3'}$ is selected from H, $C_1$-$C_{10}$-alkyl, $C_2$-$C_{10}$-alkenyl or $C_2$-$C_{10}$-alkynyl, in each case branched or unbranched, mono- or poly-substituted or unsubstituted;

alkylaryl, saturated or unsaturated, mono- or poly-substituted or unsubstituted; aryl, mono- or poly-substituted or unsubstituted;

or $R^1$ and $R^2$ together form a $C_3$-$C_7$-cycloalkyl, saturated or unsaturated, mono- or poly-substituted or unsubstituted, or a corresponding heterocycle in which a carbon atom in the ring has been replaced by S, O or $NR^{4'}$, where $R^{4'}$ is selected from H, $C_1$-$C_{10}$-alkyl, $C_2$-$C_{10}$-alkenyl or $C_3$-$C_{10}$-alkynyl, in each case branched or unbranched, mono- or poly-substituted or unsubstituted;

and $R^3$ to $R^6$, independently of one another, are selected from H or any radicals selected from the group consisting of F, Cl, Br, I, CN, $CF_3$, $OCF_3$, $NO_2$, $C_1$-$C_{10}$-alkyl, $C_2$-$C_{10}$-alkenyl and $C_3$-$C_{10}$-alkynyl, in each case branched or unbranched, mono- or poly-substituted or unsubstituted; $C_3$-$C_7$-cycloalkyl, saturated or unsaturated, mono- or poly-substituted or unsubstituted, or a corresponding heterocycle in which a carbon atom in the ring has been replaced by S, O or $NR^{5'}$, where $R^{5'}$ is selected from H, $C_1$-$C_{10}$-alkyl, $C_2$-$C_{10}$-alkenyl or $C_2$-$C_{10}$-alkynyl, in each case branched or unbranched, mono- or poly-substituted or unsubstituted;

$OR^{6'}$, $OC(O)R^{6'}$, $OC(S)R^{6'}$, $C(O)R^{6'}$, $C(O)OR^{6'}$, $C(S)R^{6'}$, $C(S)OR^{6'}$, $SR^{6'}$, $S(O)R^{6'}$ or $S(O_2)R^{6'}$, where $R^{6'}$ is selected from H, $C_1$-$C_{10}$-alkyl, $C_2$-$C_{10}$-alkenyl or $C_2$-$C_{10}$-alkynyl, in each case branched or unbranched, mono- or poly-substituted or unsubstituted; $C_3$-$C_7$-cycloalkyl, saturated or unsaturated, mono- or poly-substituted or unsubstituted, or a corresponding heterocycle in which a carbon atom in the ring has been replaced by S, O or $NR^7$, where $R^7$ is selected from H, $C_1$-$C_{10}$-alkyl, $C_2$-$C_{10}$-alkenyl or $C_3$-$C_{10}$-alkynyl, in each case branched or unbranched, mono- or poly-substituted or unsubstituted;

alkylaryl, saturated or unsaturated, mono- or poly-substituted or unsubstituted; aryl or 5- or 6-membered heteroaryl aromatic rings containing 1 or 2 heteroatoms selected from the group consisting of O, N and S, in each case mono- or poly-substituted or unsubstituted;

$NR^8R^9$, $C(O)NR^8R^9$ or $S(O_2)NR^8R^9$ wherein $R^8$ and $R^9$, independently of one another, are selected from H, $C_1$-$C_{18}$-alkyl, $C_2$-$C_{18}$-alkenyl or $C_3$-$C_{18}$-alkynyl, in each case branched or unbranched, mono- or poly-substituted or unsubstituted; $C_3$-$C_7$-cycloalkyl, saturated or unsaturated, mono- or poly-substituted or unsubstituted, or a corresponding heterocycle in which a carbon atom in the ring has been replaced by S, O or $NR^{10}$, where $R^{10}$ is selected from H, $C_1$-$C_{10}$-alkyl, $C_2$-$C_{10}$-alkenyl or $C_3$-$C_{10}$-alkynyl, in each case branched or unbranched, mono- or poly-substituted or unsubstituted;

alkylaryl, saturated or unsaturated, mono- or poly-substituted or unsubstituted; aryl or 5- or 6-membered heteroaryl aromatic rings containing 1 or 2 heteroatoms selected from the group consisting of O, N and S, in each case mono- or poly-substituted or unsubstituted;
or
$R^8$ and $R^9$ together form a $C_3$-$C_7$-cycloalkyl, saturated or unsaturated, mono- or poly-substituted or unsubstituted, or a corresponding heterocycle in which a carbon atom in the ring has been replaced by S, O or $NR^{10}$, where
$R^{10}$ is selected from H, $C_1$-$C_{10}$-alkyl, $C_2$-$C_{10}$-alkenyl or $C_3$-$C_{10}$-alkynyl, in each case branched or unbranched, mono- or poly-substituted or unsubstituted;
alkylaryl, aryl or 5- or 6-membered heteroaryl aromatic rings containing 1 or 2 heteroatoms selected from the group consisting of O, N and S, in each case mono- or poly-substituted or unsubstituted,
and
Y is selected from H and OH when X is simultaneously H, or
X and Y together form a bond,
wherein mono- or poly-substituted means the replacement of one or more hydrogens with one or more substituents selected from the group consisting of F, Cl, Br, I, $NH_2$, SH, OH, and $OCH_3$;
or a salt thereof with physiologically acceptable acid, said process comprising the steps of:
reacting a cycloalkanone of formula II with an immonium salt of formula III or with paraformaldehyde and an amine of formula IV, wherein $R^{10}$ has a meaning analogous to $R^1$ and $R^{11}$ has a meaning analogous to $R^2$,
reacting the resulting Mannich bases with an organometallic compound of formula V in which Z represents Li, in solvents at a temperature of from $-70°$ C. to $60°$ C., wherein, in the case where either $R^{10}$ or $R^{11}$ is hydrogen or $R^{10}$ and $R^{11}$ are simultaneously hydrogen, compounds of formula III or IV in which $R^{10}$ or $R^{11}$ or $R^{10}$ and $R^{11}$ represent a benzyl radical are used in the Mannich reaction, which benzyl radical is removed by catalytic reaction with hydrogen, and wherein compounds of formula V in which Z represents lithium or magnesium halide are prepared by halogen-lithium exchange by reaction of halogen compounds of formula VI in which A is Cl, Br or I, or compounds of formula V are reacted with compounds of formula II in the presence of cerium(II) halide, to yield products of the general formula VII wherein $R^{10}$ has a meaning analogous to $R^1$ and $R^{11}$ has a meaning analogous to $R^2$, which products are reacted with thionyl chloride and then subjected to basic working up to form compounds of formula IX or a mixture of compounds of formulas VIII and IX wherein $R^{10}$ has a meaning analogous to $R^1$ and $R^{11}$ has a meaning analogous to $R^2$, the compounds are separated, or
preparing compounds of formula IX by reacting compounds of formula VII with strong acids, then hydrogenolytically cleaving compounds of formula VIII or hydrogenating compounds of formula IX wherein $R^{10}$ has a meaning analogous to $R^1$ and $R^{11}$ has a meaning analogous to $R^2$ by catalytic reaction with hydrogen in solvents at pressures of from 0.1 to 10 bar and temperatures of from $20°$ C. to $80°$ C., to form compounds of formula X wherein $R^{10}$ has a meaning analogous to $R^1$ and $R^{11}$ has a meaning analogous to $R^2$.

11. The process of claim 10, wherein said halogen-lithium exchange is performed with a solution of n-butyllithium and hexane.

12. A process according to claim 10, wherein at least one OH group present in formula I is replaced by an $OSi(Ph)_2$tert.but, group, at least one SH group is replaced by a S-p-methoxybenzyl group and/or at least one $NH_2$ group is replaced by an $NO_2$ group and, when the entire reaction sequence is complete, removing a $OSi(Ph)_2$tert.but, group with tetrabutylammonium fluoride in tetrahydrofuran and/or removing at least one p-methoxybenzyl group with a metal amine, and/or reducing at least one $NO_2$ group to $NH_2$.

13. The process of claim 12, wherein said metal amine is sodium amine.

14. A process according to claim 11, wherein after the butyllithium reaction, the process further comprises the step of saponifying at least one $C(O)OCH_3$ and/or a $C(S)OCH_3$ group using KOH solution or NaOH solution in methanol at a temperature of from $40°$ C. to $60°$ C.

15. A pharmaceutical formulation comprising as an active ingredient one or more compounds corresponding to formula I

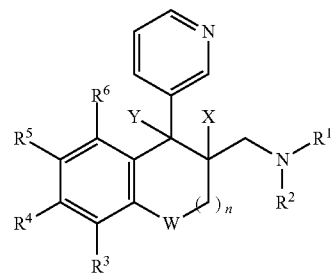

wherein
W is $CH_2$, and n=from 0 to 3,
$R^1$ and $R^2$, independently of one another, are selected from H, $C_1$-$C_{10}$-alkyl, $C_2$-$C_{10}$-alkenyl or $C_3$-$C_{10}$-alkynyl, in each case branched or unbranched, mono- or poly-substituted or unsubstituted; $C_3$-$C_7$-cycloalkyl, saturated or unsaturated, mono- or poly-substituted or unsubstituted, or a corresponding heterocycle in which a carbon atom in the ring has been replaced by S, O or $NR^{3'}$, where $R^{3'}$ is selected from
H, $C_1$-$C_{10}$-alkyl, $C_2$-$C_{10}$-alkenyl or $C_2$-$C_{10}$-alkynyl, in each case branched or unbranched, mono- or poly-substituted or unsubstituted;
alkylaryl, saturated or unsaturated, mono- or poly-substituted or unsubstituted; aryl, mono- or poly-substituted or unsubstituted;
or
$R^1$ and $R^2$ together form a $C_3$-$C_7$-cycloalkyl, saturated or unsaturated, mono- or poly-substituted or unsubstituted, or a corresponding heterocycle in which a carbon atom in the ring has been replaced by S, O or $NR^{4'}$, where
$R^{4'}$ is selected from H, $C_1$-$C_{10}$-alkyl, $C_2$-$C_{10}$-alkenyl or $C_3$-$C_{10}$-alkynyl, in each case branched or unbranched, mono- or poly-substituted or unsubstituted;
and
$R^3$ to $R^6$, independently of one another, are selected from H or any radicals selected from the group consisting of F, Cl, Br, I, CN, $CF_3$, $OCF_3$, $NO_2$, $C_1$-$C_{10}$-alkyl, $C_2$-$C_{10}$-alkenyl and $C_3$-$C_{10}$-alkynyl, in each case branched or unbranched, mono- or poly-substituted or unsubstituted; $C_3$-$C_7$-cycloalkyl, saturated or unsaturated, mono- or poly-substituted or unsubstituted, or a corresponding heterocycle in which a carbon atom in the ring has been replaced by S, O or $NR^{5'}$, where $R^{5'}$ is selected from H, $C_1$-$C_{10}$-alkyl, $C_2$-$C_{10}$-alkenyl or $C_2$-$C_{10}$-alkynyl, in each case branched or unbranched, mono- or poly-substituted or unsubstituted;

$OR^{6'}$, $OC(O)R^{6'}$, $OC(S)R^{6'}$, $C(O)R^{6'}$, $C(O)OR^{6'}$, $C(S)R^{6'}$, $C(S)OR^{6'}$, $SR^{6'}$, $S(O)R^{6'}$ or $S(O_2)R^{6'}$, where $R^{6'}$ is selected from H, $C_1$-$C_{10}$-alkyl, $C_2$-$C_{10}$-alkenyl or $C_2$-$C_{10}$-alkynyl, in each case branched or unbranched, mono- or poly-substituted or unsubstituted; $C_3$-$C_7$-cycloalkyl, saturated or unsaturated, mono- or poly-substituted or unsubstituted, or a corresponding heterocycle in which a carbon atom in the ring has been replaced by S, O or $NR^7$, where $R^7$ is selected from H, $C_1$-$C_{10}$-alkyl, $C_2$-$C_{10}$-alkenyl or $C_3$-$C_{10}$-alkynyl, in each case branched or unbranched, mono- or poly-substituted or unsubstituted;

alkylaryl, saturated or unsaturated, mono- or poly-substituted or unsubstituted; aryl or 5- or 6-membered heteroaryl aromatic rings containing 1 or 2 heteroatoms selected from the group consisting of O, N and S, in each case mono- or poly-substituted or unsubstituted;

$NR^8R^9$, $C(O)NR^8R^9$ or $S(O_2)NR^8R^9$ wherein $R^8$ and $R^9$, independently of one another, are selected from H, $C_1$-$C_{18}$-alkyl, $C_2$-$C_{18}$-alkenyl or $C_3$-$C_{18}$-alkynyl, in each case branched or unbranched, mono- or poly-substituted or unsubstituted; $C_3$-$C_7$-cycloalkyl, saturated or unsaturated, mono- or poly-substituted or unsubstituted, or a corresponding heterocycle in which a carbon atom in the ring has been replaced by S, O or $NR^{10}$, where $R^{10}$ is selected from H, $C_1$-$C_{10}$-alkyl, $C_2$-$C_{10}$-alkenyl or $C_3$-$C_{10}$-alkynyl, in each case branched or unbranched, mono- or poly-substituted or unsubstituted;

alkylaryl, saturated or unsaturated, mono- or poly-substituted or unsubstituted; aryl or 5- or 6-membered heteroaryl aromatic rings containing 1 or 2 heteroatoms selected from the group consisting of O, N and S, in each case mono- or poly-substituted or unsubstituted;

or $R^8$ and $R^9$ together form a $C_3$-$C_7$-cycloalkyl, saturated or unsaturated, mono- or poly-substituted or unsubstituted, or a corresponding heterocycle in which a carbon atom in the ring has been replaced by S, O or $NR^{10}$, where $R^{10}$ is selected from H, $C_1$-$C_{10}$-alkyl, $C_2$-$C_{10}$-alkenyl or $C_3$-$C_{10}$-alkynyl, in each case branched or unbranched, mono- or poly-substituted or unsubstituted;

alkylaryl, aryl or 5- or 6-membered heteroaryl aromatic rings containing 1 or 2 heteroatoms selected from the group consisting of O, N and S, in each case mono- or poly-substituted or unsubstituted, and Y is selected from H and OH when X is simultaneously H, or X and Y together form a bond, wherein mono- or poly-substituted means the replacement of one or more hydrogens with one or more substituents selected from the group consisting of F, Cl, Br, I, $NH_2$, SH, OH, and $OCH_3$;

or a pharmaceutically acceptable salt thereof, and a pharmaceutically acceptable auxiliary substance.

16. A method for the treatment or inhibition of pain, depression and/or anxiety in a mammal, said method comprising the step of administering to said mammal a pharmaceutically effective amount of a compound corresponding to formula I of claim 1 or a pharmaceutically acceptable salt thereof.

17. A method for the treatment or inhibition of a condition selected from the group consisting of migraine, urinary incontinence, fibromyalgia, eating disorders, bulimia, hyperactivity, drug dependency, addiction or withdrawal, trichotillomania, Tourette's syndrome, skin, psychoses, memory disorders, cognitive disorders and Alzheimer's disease in a mammal, said method comprising the step of administering to said mammal a pharmaceutically effective amount of a compound corresponding to formula I of claim 1 or a pharmaceutically acceptable salt thereof.

18. The method of claim 17, wherein said skin disorder is post-herpetic neuralgia or pruritus.

* * * * *